(12) United States Patent
Shook et al.

(10) Patent No.: US 10,398,706 B2
(45) Date of Patent: Sep. 3, 2019

(54) HETEROARYLDIAZEPINE DERIVATIVES AS RSV INHIBITORS

(71) Applicant: Enanta Pharmaceuticals, Inc., Watertown, MA (US)

(72) Inventors: Brian C. Shook, Holliston, MA (US); In Jong Kim, Lexington, MA (US); Jianming Yu, Plainsboro, NJ (US); Thomas P. Blaisdell, Brighton, MA (US); Joseph Panarese, Malden, MA (US); Yat Sun Or, Watertown, MA (US)

(73) Assignee: Enanta Pharmaceuticals, Inc., Watertown, MA (US)

(*) Notice: Subject to any disclaimer, the term of this patent is extended or adjusted under 35 U.S.C. 154(b) by 0 days.

(21) Appl. No.: 15/863,216

(22) Filed: Jan. 5, 2018

(65) Prior Publication Data

US 2018/0193352 A1    Jul. 12, 2018

Related U.S. Application Data

(60) Provisional application No. 62/443,165, filed on Jan. 6, 2017.

(51) Int. Cl.
| | |
|---|---|
| A61K 31/551 | (2006.01) |
| C07D 495/04 | (2006.01) |
| C07D 471/04 | (2006.01) |
| C07D 487/04 | (2006.01) |
| C07D 491/04 | (2006.01) |
| C07D 498/04 | (2006.01) |
| C07D 513/04 | (2006.01) |
| A61P 31/14 | (2006.01) |

(52) U.S. Cl.
CPC ............ *A61K 31/551* (2013.01); *A61P 31/14* (2018.01); *C07D 471/04* (2013.01); *C07D 495/04* (2013.01)

(58) Field of Classification Search
CPC .. A61K 31/551; C07D 495/04; C07D 471/04; C07D 487/04; C07D 491/04; C07D 498/04; C07D 513/04
USPC .................. 514/221; 540/502, 503
See application file for complete search history.

(56) References Cited

U.S. PATENT DOCUMENTS

| | | |
|---|---|---|
| 5,571,809 A | 11/1996 | Hargrave et al. |
| 9,732,098 B2 | 8/2017 | Hunt et al. |
| 9,957,281 B2 | 5/2018 | Shook et al. |
| 2006/0083741 A1 | 4/2006 | Hoffman et al. |
| 2007/0142403 A1 | 6/2007 | Powell et al. |
| 2007/0185094 A1 | 8/2007 | Lattmann et al. |
| 2007/0185096 A1 | 8/2007 | Powell et al. |
| 2008/0139536 A1 | 6/2008 | Dowdell et al. |
| 2010/0015063 A1 | 1/2010 | Carter et al. |
| 2012/0196846 A1 | 8/2012 | Mackman et al. |
| 2014/0038947 A1 | 2/2014 | Glick et al. |
| 2015/0065504 A1 | 3/2015 | Wang et al. |
| 2015/0299210 A1 | 10/2015 | Bailey et al. |
| 2017/0226129 A1 | 8/2017 | Yu et al. |
| 2017/0355717 A1 | 12/2017 | Hunt et al. |
| 2018/0237425 A1 | 8/2018 | Kim et al. |
| 2018/0258102 A1 | 9/2018 | Shook et al. |

FOREIGN PATENT DOCUMENTS

| | | |
|---|---|---|
| WO | 2006081389 A1 | 8/2006 |
| WO | 2014047369 A1 | 3/2014 |
| WO | 2014125444 A1 | 8/2014 |
| WO | 2014184350 A1 | 11/2014 |
| WO | 2016097761 A1 | 4/2016 |
| WO | 20160554792 A1 | 4/2016 |

OTHER PUBLICATIONS

Xiong, et al., "Discover of a potent respiratory syncytial virus RNA polymerase inhibitor," Bioorganic & Medicinal Chemistry Letters, 23:6789-6793, 2013.
Carter, et al., "1,4-Benzodiazepines as Inhibitors of Respiratory Syncytial Virus," Journal of Medicinal Chemistry, 49:2311-2319, 2006.
Henderson, et al., "1,4-Benzodiazepines as Inhibitors of Respiratory Syncytial Virus, The Identification of Clinical Candidate," Journal of Medicinal Chemistry, 50:1685-1692, 2007.
Albright, et al. (Document No. 130:153583) retrieved from STN; entered in STN on Feb. 16, 1999.
Albright, et al. (Document No. 129:54301) retrieved from STN; entered in STN on Jun. 17, 1998.
Lee, et al. (Document No. 140:69941) retrieved from STN; entered in STN on Jul. 8, 2003.
Zheng, et al. (Document No. 161 :399872) retrieved from STN; entered in STN on Jul. 23, 2014.

(Continued)

*Primary Examiner* — Brenda L Coleman
(74) *Attorney, Agent, or Firm* — Elmore Patent Law Group, P.C.; Edgar W. Harlan; Carolyn S. Elmore

(57) ABSTRACT

The present invention discloses compounds of Formula (I), and pharmaceutically acceptable salts, esters, or prodrugs thereof:

(I)

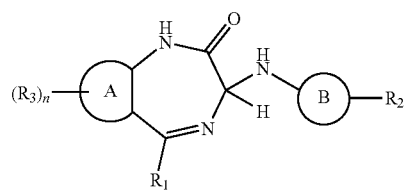

These compounds are useful for treating Respiratory Syncytial Virus (RSV) infection. The present invention further relates to pharmaceutical compositions comprising these compounds for administration to a subject suffering from RSV infection. The invention also relates to methods of treating an RSV infection in a subject by administering to the subject a pharmaceutical composition comprising a compound of the invention.

11 Claims, No Drawings

(56) References Cited

OTHER PUBLICATIONS

Wang, et al. (Document No. 160:385666) retrieved from STN; entered in STN on Feb. 27, 2014.
Xiong, et al. (Document No. 160:101182) retrieved from STN; entered in STN on Nov. 12, 2013.
Heeney, et al. (Document No. 153:359062) retrieved from STN; entered in STN on Sep. 2, 2010.
Andrzej, et al. (Document No. 144:274313) retrieved from STN; entered in STN on Mar. 3, 2006.
Peesapati, et al. (Document No. 120:244848) retrieved from STN; entered in STN on May 14, 1994.
Respiratory syncytial virus (RSV) [online], retrieved from from internet on Jun. 25, 2017.; URL http://www.mayoclinic.org/diseases-condiitons/respiratory-syncytial-virus/basics/prevention.
U.S. Appl. No. 16/001,247, filed Jun. 6, 2018.

HETEROARYLDIAZEPINE DERIVATIVES AS RSV INHIBITORS

RELATED APPLICATION

This application claims the benefit of U.S. Provisional Application No. 62/443,165 filed on Jan. 6, 2017. The entire teachings of the above application are incorporated herein by reference.

TECHNICAL FIELD

The present invention relates generally to compounds and pharmaceutical compositions useful as Respiratory Syncytial Virus (RSV) inhibitors. Specifically, the present invention relates to benzodiazepine derivatives that can inhibit RSV activities and for treating RSV infection.

BACKGROUND OF THE INVENTION

Human respiratory syncytial virus (HRSV) is a negative-sense, single stranded, RNA paramyxovirus (K M. Empey, et al., *Rev. Anti-Infective Agents,* 2010, 50(1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, and *J. Med. Chem.* 2015, 58, 1630-1643. Examples of other N-protein inhibitors for treatment of HRSV have been disclosed in the following publications: WO 2004/026843, *J. Med. Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2013/242525 and *J. Med. Chem.* 2015, 58, 1862-1878.

There is a need for the development of effective treatments for HRSV.

SUMMARY OF THE INVENTION

The present invention provides compounds represented by Formula (I), and pharmaceutically acceptable salts, esters and prodrugs thereof, which are useful for treating or preventing viral (particularly HRSV) infection:

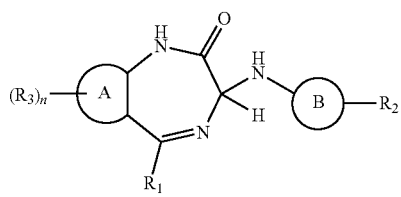

wherein:
A is heteroaryl;
B is selected from the group consisting of:

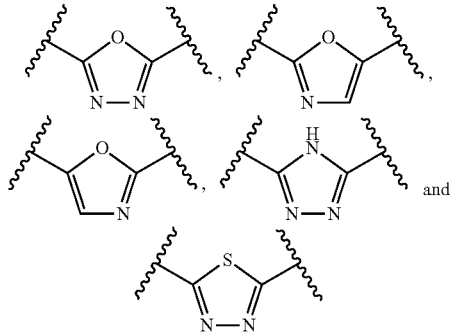

$R_1$ is optionally substituted aryl or optionally substituted heteroaryl;
$R_2$ is selected from the group consisting of:
1) Optionally substituted —$C_3$-$C_{12}$ cycloalkyl;
2) Optionally substituted —$C_3$-$C_{12}$ cycloalkenyl;
3) Optionally substituted 3- to 12-membered heterocyclyl;
4) Optionally substituted aryl;
5) Optionally substituted heteroaryl;
6) —$NR_{13}R_{14}$;
7) —CO—$NR_{13}R_{14}$; and
8) —$SO_2$—$NR_{13}R_{14}$;

Each $R_3$ is independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —$NHC_1$-$C_8$ alkyl, optionally substituted —S—(—$C_1$-$C_8$ alkyl), optionally substituted —$SO_2$—(—$C_1$-$C_8$ alkyl), optionally substituted —$SO_2$—NH—(—$C_1$-$C_8$ alkyl), optionally substituted —NH—$SO_2$—(—$C_1$-$C_8$ alkyl), —$CO_2R_{11}$, —$NR_{13}R_{14}$, and —$C(O)NR_{13}R_{14}$;

Each $R_{11}$ is independently selected from the group consisting of:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_8$ cycloalkyl;
5) Optionally substituted —$C_3$-$C_8$ cycloalkenyl;
6) Optionally substituted 3- to 8-membered heterocycloalkyl;

7) Optionally substituted aryl; and
8) Optionally substituted heteroaryl;

$R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted —$C_1$-$C_8$-alkoxy, —C(O)$R_{11}$, —S(O)$_2R_{11}$, and —S(O)$_2$NH$R_{11}$; alternatively, $R_{13}$ and $R_{14}$ are taken together with the nitrogen atom to which they are attached to form an optionally substituted heterocyclic ring;

n is 0 to k, where k is the total number of CH and NH groups in the heteroaryl group A when A is unsubstituted; preferably, n is 0, 1 or 2.

Each preferred group stated above can be taken in combination with one, any or all other preferred groups.

DETAILED DESCRIPTION OF THE INVENTION

In one embodiment, the present invention provides compound represented by Formula (I) as described above, or a pharmaceutically acceptable salt, ester or prodrug thereof.

The carbon atom at position 3 of the benzodiazepine ring system of the compounds of the invention is chiral. Thus, compounds of the invention can have the stereochemistry depicted in Formula (Ia) or (Ib):

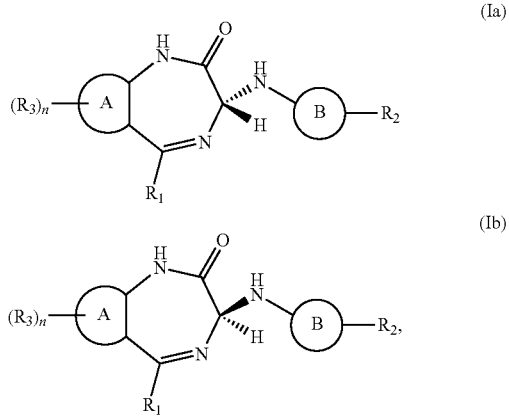

wherein $R_1$, $R_2$, $R_3$, A, B and n are previously defined. A composition of the invention can comprise a compound of the invention as a racemic mixture of Formula (Ia) and Formula (Ib), a pure enantiomer of either Formula (Ia) or Formula (Ib), or an excess of one enantiomer over the other. For example, the composition can comprise the compound in an enantiomeric excess of at least 5, 10, 20, 30, 40, 50, 60, 70, 80 or 90%. In one embodiment, the enantiomeric excess is at least 95%. In compounds of the invention having two or more chiral atoms, such compounds can be present in a composition as a pure stereoisomer or a mixture of stereoisomers, such as a racemic mixture or a mixture of diastereomers. In one embodiment, a composition of the invention comprises a racemic mixture, a single stereoisomer or enantiomers with one enantiomer present in an enantiomeric excess of at least 5, 10, 20, 30, 40, 50, 60, 70, 80, 90 or 95%.

In a preferred embodiment, a compound of the invention is represented by Formula (Ib). Compositions of the invention preferably comprise a substantially pure compound of Formula (Ib), or a mixture of a compound of Formula (Ib) and the corresponding compound of Formula (Ia), with an enantiomeric excess of the compound of Formula (Ib) as discussed above.

In certain embodiments, the present invention relates to compounds of Formula (I), and pharmaceutically acceptable salts thereof, wherein $R_1$ is optionally substituted aryl. In certain embodiments, the present invention relates to compounds of Formula (I), and pharmaceutically acceptable salts thereof, wherein $R_1$ is optionally substituted heteroaryl. Preferably $R_1$ is phenyl optionally substituted with one to three substituents selected from the group consisting of halo, —CF$_3$, —OCF$_3$, —CH$_3$, —SO$_2$Me, and cyano. In certain embodiments, $R_1$ is unsubstituted phenyl.

In certain embodiments, the present invention relates to compounds of Formula (I), and pharmaceutically acceptable salts thereof, wherein A is monocyclic 5-membered heteroaryl. In one embodiment, the present invention relates to compounds of Formula (I), and pharmaceutically acceptable salts thereof, wherein A is an optionally substituted five-membered sulfur containing heteroaryl group, such as a thieno, thiazolo or thiadiazolo group.

In certain embodiments, the present invention relates to compounds of Formula (I), and pharmaceutically acceptable salts thereof, wherein A is derived from one of the following by removal of the hydrogen atoms from two adjacent ring carbon atoms:

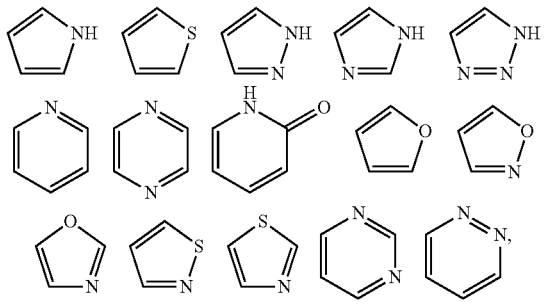

wherein each of the above shown monocyclic heteroaryl groups is optionally substituted with n $R_3$ groups. Preferably, each $R_3$ group is independently selected from halo, —CH$_3$, —CF$_3$, —OCF$_3$, —CN, —SO$_2$CH$_3$, —CH$_2$N(CH$_3$)$_2$, —C$_1$-C$_8$-alkoxy, —C$_1$-C$_8$-alkyl, and —C(O)CH$_3$. It is to be understood that depending on the heteroaryl group, n can be 0, 1, 2 or 3. In preferred embodiments, n is 0, 1 or 2.

In certain embodiments, $R_2$ is an optionally substituted aryl, heteroaryl, 3- to 12-membered heterocycloalkyl, —C$_3$-C$_{12}$-cycloalkyl, —C$_3$-C$_{12}$ cycloalkenyl, aryl-O—, heteroaryl-O, aryl-C$_1$-C$_4$-alkyl or heteroaryl-C$_1$-C$_4$-alkyl. In certain embodiments, $R_2$ is phenyl, naphthyl, 5-membered heteroaryl or 6-membered heteroaryl, each of which is optionally substituted. In certain embodiments, $R_2$ is a 5- or 6-membered heteroaryl fused with a 6-membered aryl, heteroaryl, carbocyclic or heterocyclic ring, such as a benzo-fused-5- or 6-membered heteroaryl or a pyrido-fused 5- or 6-membered heteroaryl.

In certain embodiments of the compounds of the invention, $R_2$ is a group derived from one of the following by removal of one hydrogen atom:

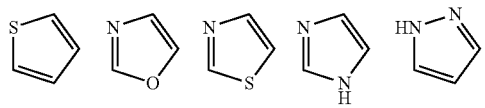

-continued

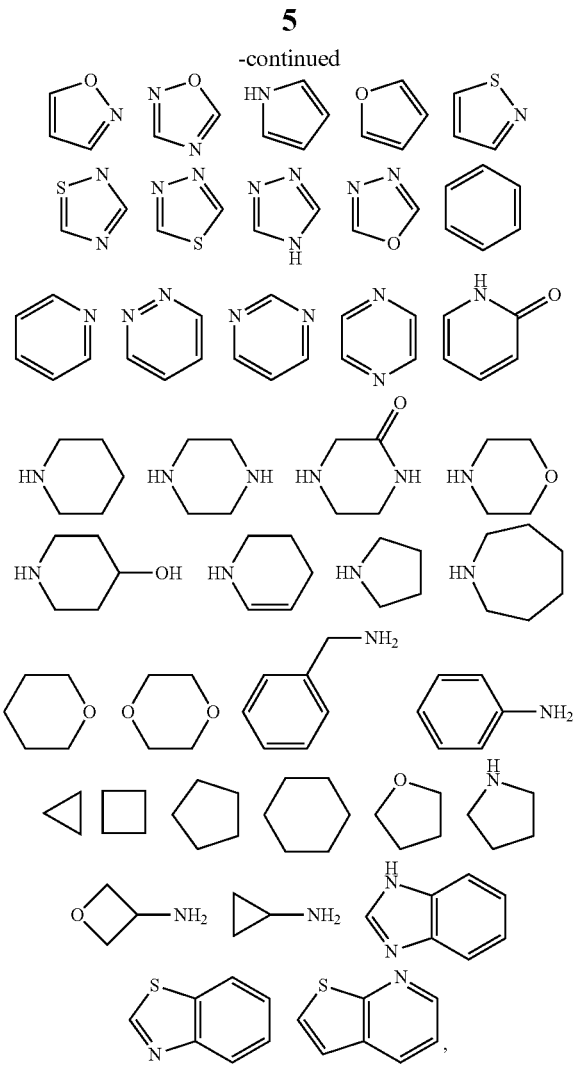

wherein each of the above shown groups is optionally substituted.

In certain embodiments, $R_2$ is selected from the groups shown below, each of which is optionally substituted:

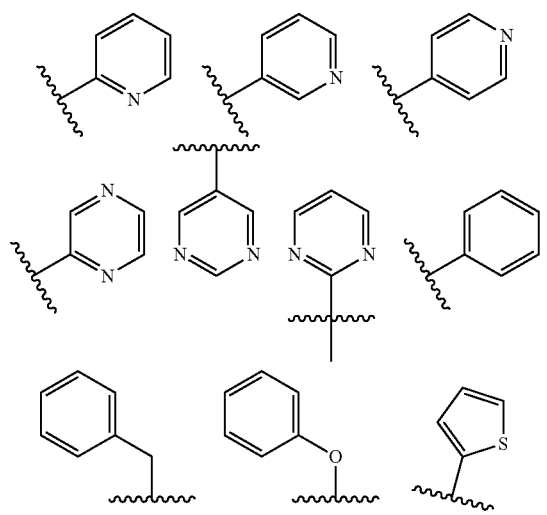

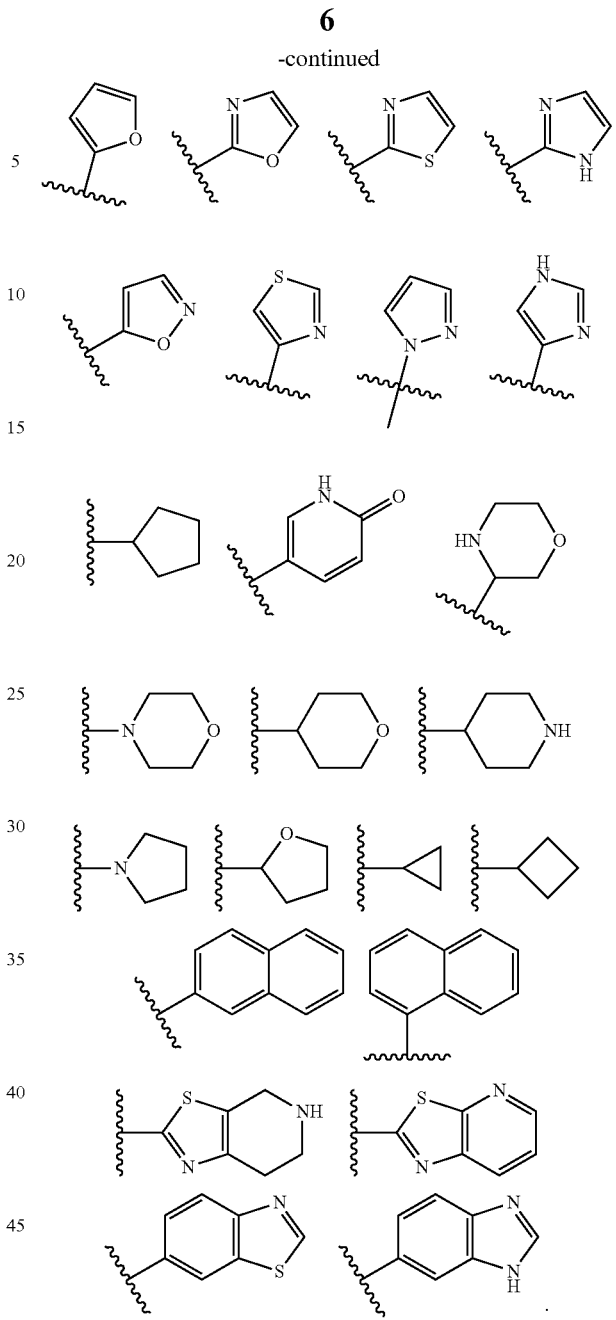

In certain embodiments, $R_2$ is substituted with one or more substituents independently selected from halo, —$CH_3$, —$CF_3$, —$OCF_3$, —CN, —$NH_2$, —OH, —$CH_2N(CH_3)_2$, —C(O)$CH_3$, —NH—($C_1$-$C_6$)alkyl, —$SO_2$—($C_1$-$C_6$)alkyl, —$SO_2$—NH—($C_1$-$C_6$)alkyl, —NH—$SO_2$—($C_1$-$C_6$)alkyl, and —$C_1$-$C_8$-alkoxy. In another embodiment, the substituents are independently selected from fluoro, chloro, $CH_3O$—, $CH_3C(O)$—, $CH_3OCH_2$—, and $CH_3OCH_2CH_2O$—.

In certain embodiments, $R_2$ is substituted with one or more substituents which are independently selected from aryl, heteroaryl, 3- to 12-membered heterocycloalkyl, $C_3$-$C_{12}$-cycloalkyl, $C_3$-$C_{12}$ cycloalkenyl, aryl-O—, heteroaryl-O, aryl-$C_1$-$C_4$-alkyl and heteroaryl-$C_1$-$C_4$-alkyl, each of which is optionally substituted, preferably with one or more methyl groups.

Preferably, at least one of the substituents is selected from the groups below:

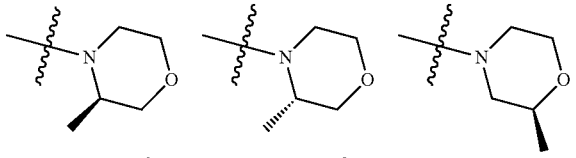
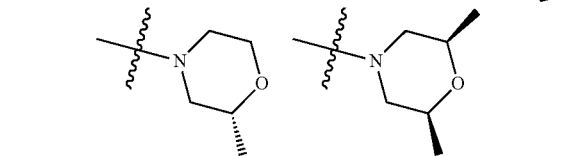
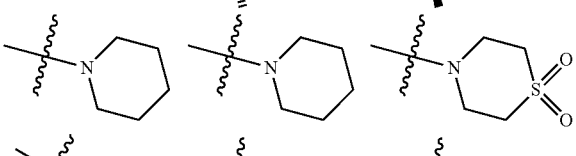
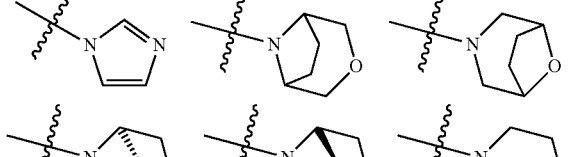

In certain embodiments, $R_2$ is substituted with a first substituent selected from halo, —$CH_3$, —$CF_3$, —$OCF_3$, —CN, —$NH_2$, —OH, —$CH_2N(CH_3)_2$, —$C(O)CH_3$, —NH—($C_1$-$C_6$)alkyl, —$SO_2$—($C_1$-$C_6$)alkyl, —$SO_2$—NH—($C_1$-$C_6$)alkyl, —NH—$SO_2$—($C_1$-$C_6$)alkyl, and —$C_1$-$C_8$-alkoxy; and a second substituent selected from aryl, heteroaryl, 3- to 12-membered heterocycloalkyl, $C_3$-$C_{12}$-cycloalkyl, $C_3$-$C_{12}$ cycloalkenyl, aryl-O—, heteroaryl-O, aryl-$C_1$-$C_4$-alkyl or heteroaryl-$C_1$-$C_4$-alkyl, each of which is optionally substituted, preferably with one or more methyl groups. Preferably, the first substituent is fluoro, chloro, $CH_3O$—, $CH_3C(O)$—, $CH_3OCH_2$—, or $CH_3OCH_2CH_2O$—. Preferably, the second substituent is one of the groups set forth below:

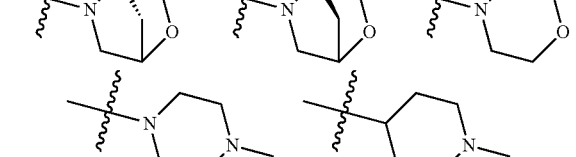
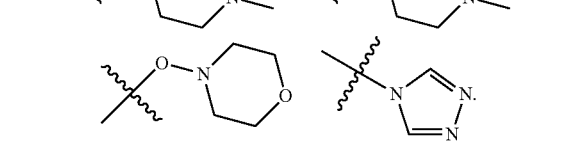
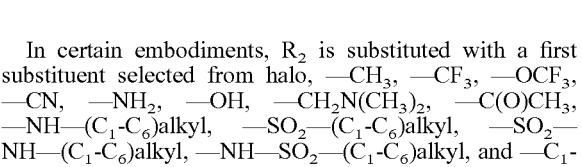

-continued

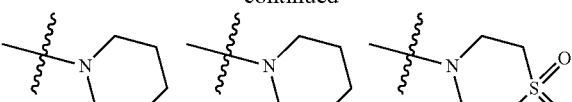
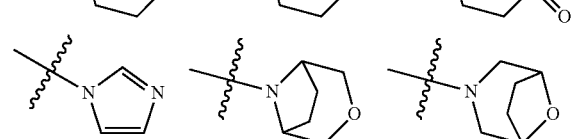
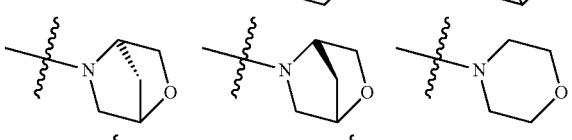
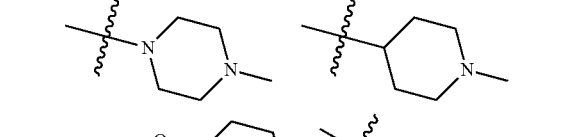
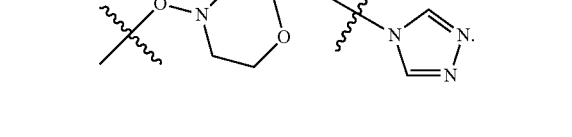

In certain embodiments $R_2$ is substituted with a first substituent selected from fluoro and $CF_3$ and a second substituent which is

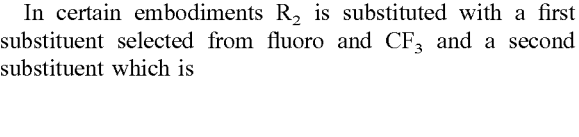

In certain embodiments, there are 0 to 4, 0 to 3, 0 to 2, 1 or 0 substituents on $R_2$. Preferably, there are 0 to 2 substituents.

In certain embodiments, $R_2$ is selected from the groups set forth below.

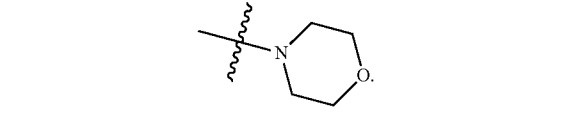 [SMILES: *N1CCOCC1]

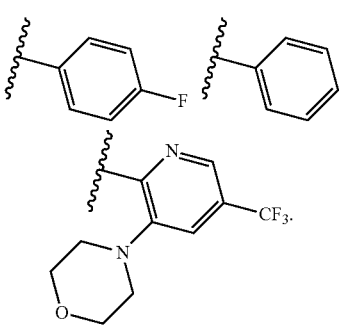

In certain embodiments of the compounds of the invention, B is one of the groups below:

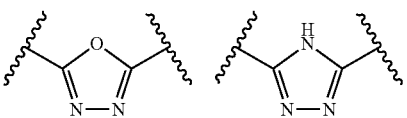

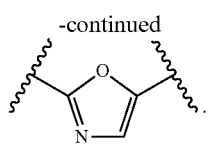

Preferably, B is

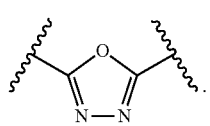 [SMILES: *c1nnc(*)o1 ; "."]

In certain embodiments of the compounds of the invention, each $R_3$ is independently halo, optionally substituted —$C_1$-$C_4$-alkyl, —$C_1$-$C_4$-alkoxy, CN or $CF_3$. Preferably each $R_3$ is methyl. In certain embodiments, n is 0 to 3, 0 to 2, 1 or 0. More preferably, n is 0.

In certain embodiments of the compounds of the invention, A is a monocyclic 5-membered heteroaryl, and n is 0, 1 or 2. Preferably the $R_3$ groups are independently selected from the group consisting of halo, $CF_3$, $OCF_3$, $SO_2Me$, cyano, optionally substituted —$C_1$-$C_8$-alkoxy, and optionally substituted methyl. Preferably A is thiophenyl; $R_1$ is optionally substituted aryl; $R_2$ is optionally substituted aryl or optionally substituted heteroaryl; n is 0, 1 or 2; each $R_3$ is methyl; and B is triazolyl, oxadiazolyl, or thiadiazolyl. Preferably B is 1,3,4-oxadiazolyl.

In certain embodiments of the compounds of the invention, A is a monocyclic 6-membered heteroaryl, and n is 0, 1 or 2. Each $R_3$ is preferably independently selected from the group consisting of halo, $CF_3$, $OCF_3$, $SO_2Me$, cyano, optionally substituted —$C_1$-$C_8$-alkoxy, and optionally substituted methyl. Preferably A is pyridyl; $R_1$ is optionally substituted aryl; $R_2$ is optionally substituted aryl or optionally substituted heteroaryl; each $R_3$ is methyl; and B is triazolyl, oxadiazolyl, or thiadiazolyl. Preferably B is 1,3,4-oxadiazolyl.

In another embodiment of the invention is a compound represented by Formula (IIa-1) or (IIb-1) or a pharmaceutically acceptable salt, ester or prodrug thereof:

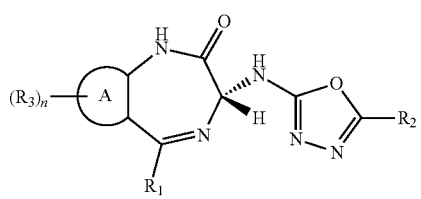

(IIa)

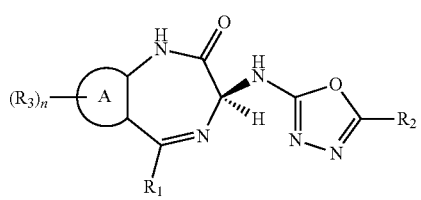

(IIb)

wherein $R_1$, $R_2$, $R_3$, A and n are as previously defined.

In another embodiment of the invention is a compound represented by one of Formulas (III-1)~(III-3), (IIIa-1)~(IIIa-3), and (IIIb-1)~(IIIb-3), or a pharmaceutically acceptable salt, ester or prodrug thereof:

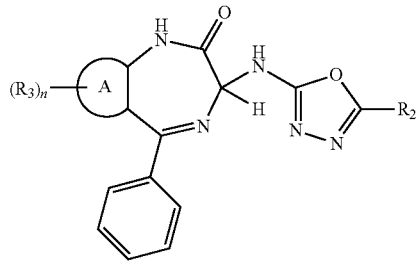

III-1

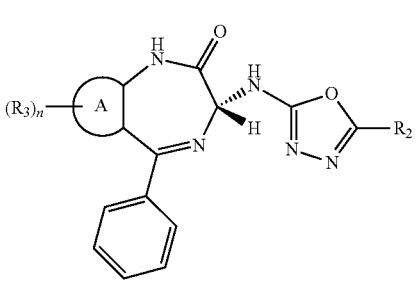

IIIa-1

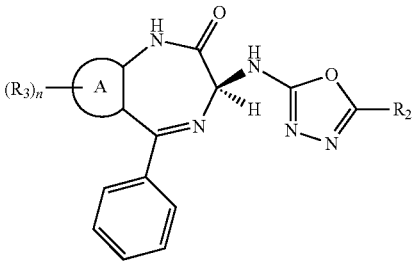

IIIb-1

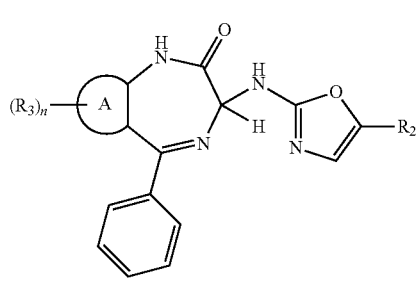

III-2

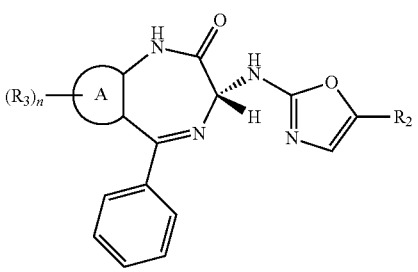

IIIa-2

-continued

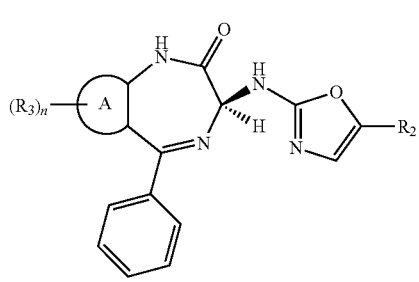
IIIb-2

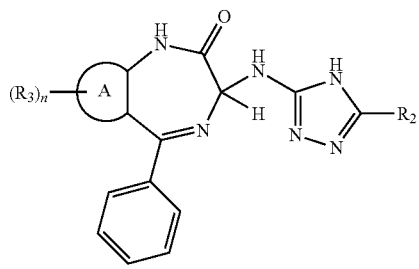
III-3

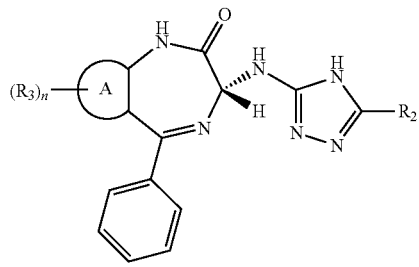
IIIa-3

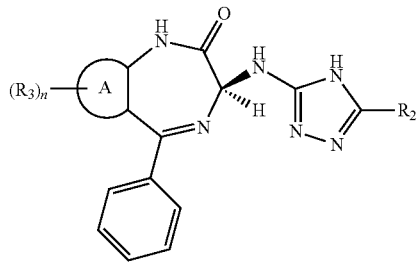
IIIb-3 wherein R$_2$, R$_3$, A and n are as previously defined. Each R$_3$ is preferably independently methyl; halo, such as fluoro or chloro; —CN; —OH; —NH$_2$; methoxy; substituted methoxy, such as trifluoromethoxy; or optionally substituted methyl, such as trifluoromethyl.

In certain embodiments, the invention provides a compound represented by Formula (IVa-1), (IVa-2), (IVb-1) or (IVb-2), or a pharmaceutically acceptable salt, ester or prodrug thereof:

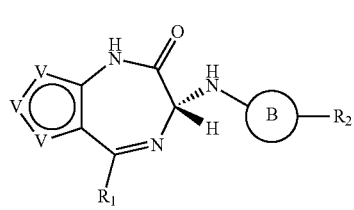
(IVa-1)

-continued

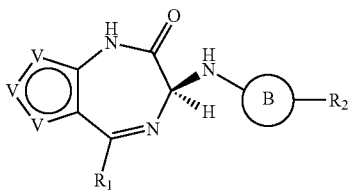
(IVa-2)

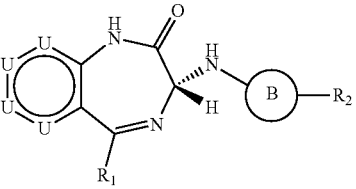
(IVb-1)

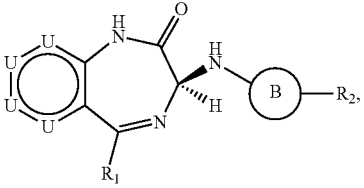
(IVb-2)

wherein one V is S, O, or NR$_{15}$, the other two Vs are independently CR$_{15}$ or N; one U is N, another U is CR$_{15}$, and the other two Us are independently CR$_{15}$ or N; R$_{15}$ is H or R$_3$; and R$_1$, R$_2$, R$_3$, and B are as previously defined.

In particular embodiments, R$_2$ for each Formula (III-1)~(III-3), (IIIa-1)~(IIIa-3), (IIIb-1)~(IIIb-3), (IVa-1)), (IVa-2), (IVb-1) and (IVb-2), is selected from the groups set forth in Table 1 (Entry 1 to Entry 184 in Table 1) and are optionally further substituted.

TABLE 1

| Entry | R$_2$ |
|---|---|
| 1 | phenyl |
| 2 | 2-fluorophenyl |
| 3 | 3-fluorophenyl |
| 4 | 4-fluorophenyl |

TABLE 1-continued
| Entry | R₂ |
|---|---|
| 5 | 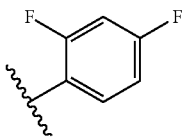 [SMILES: *c1ccc(F)cc1F] |
| 6 | 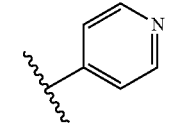 |
| 7 | 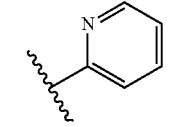 [SMILES: *c1ccccn1] |
| 8 | 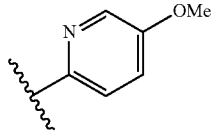 [SMILES: *c1ccc(OC)cn1] |
| 9 | 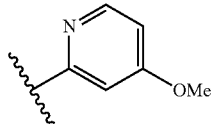 [SMILES: *c1cc(OC)ccn1] |
| 10 | 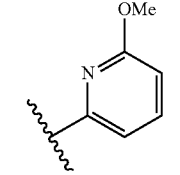 [SMILES: *c1cccc(OC)n1] |
| 11 | 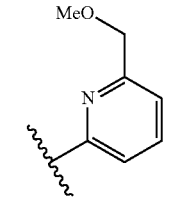 [SMILES: *c1cccc(COC)n1] |
| 12 | 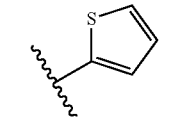 [SMILES: *c1cccs1] |
| 13 | 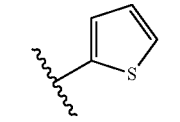 [SMILES: *c1cccs1] |
| 14 | 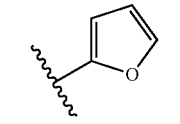 |
TABLE 1-continued
| Entry | R₂ |
|---|---|
| 15 | 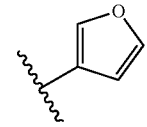 |
| 16 | 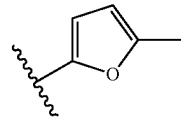 [SMILES: *c1ccc(C)o1] |
| 17 | 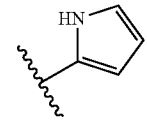 |
| 18 | 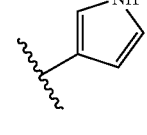 |
| 19 | 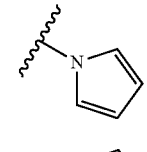 |
| 20 | 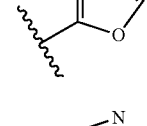 |
| 21 | 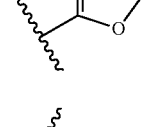 |
| 22 | 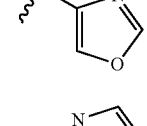 |
| 23 | 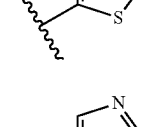 |
| 24 | 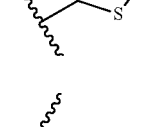 |
| 25 | 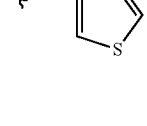 |

TABLE 1-continued
| Entry | R₂ |
|---|---|
| 26 | 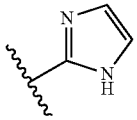 [SMILES: *c1ncc[nH]1] |
| 27 | 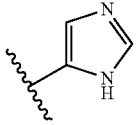 |
| 28 | 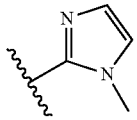 |
| 29 | 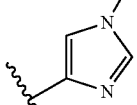 |
| 30 | 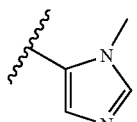 |
| 31 | 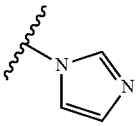 [SMILES: *n1ccnc1] |
| 32 | 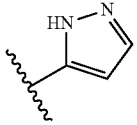 [SMILES: *c1ccn[nH]1] |
| 33 | 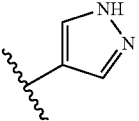 [SMILES: *c1cn[nH]c1] |
| 34 | 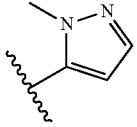 [SMILES: *c1ccnn1C] |
| 35 | 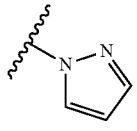 [SMILES: *n1cccn1] |
| 36 | 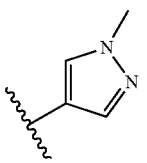 [SMILES: *c1cnn(C)c1] |
| 37 | 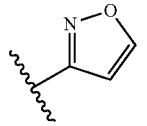 [SMILES: *c1ccon1] |
| 38 | 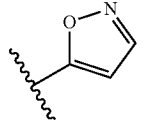 [SMILES: *c1ccno1] |
| 39 | 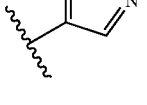 |
| 40 | 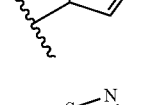 |
| 41 | 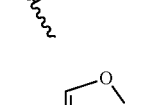 |
| 42 | 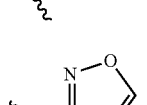 |
| 43 | 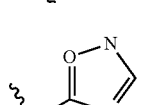 |
| 44 | 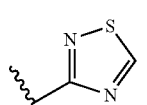 |
| 45 | 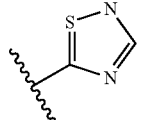 |
| 46 | 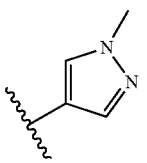 [SMILES: *c1cnn(C)c1] |

TABLE 1-continued
| Entry | R₂ |
|---|---|
| 47 | 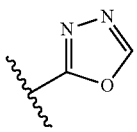 |
| 48 | 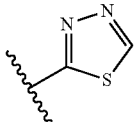 [SMILES: *c1nncs1] |
| 49 | 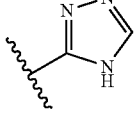 |
| 50 | 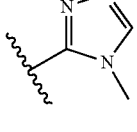 |
| 51 | 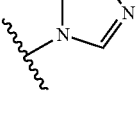 |
| 52 | 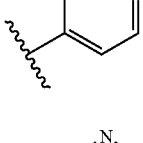 |
| 53 | 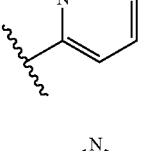 |
| 54 | 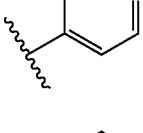 |
| 55 | 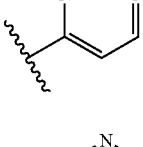 |
| 56 | 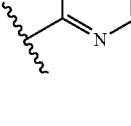 |
| 57 | 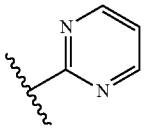 |
| 58 | 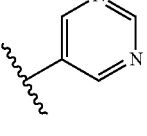 |
| 59 | 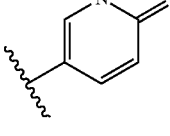 |
| 60 | 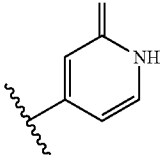 |
| 61 | 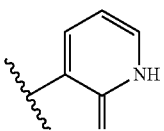 |
| 62 | 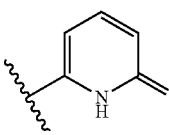 |
| 63 | 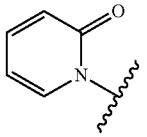 [SMILES: *n1ccccc1=O] |
| 64 | 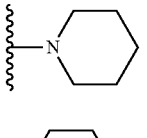 |
| 65 | 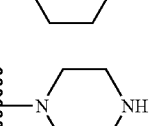 |
| 66 | 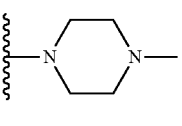 |
| 67 |  |

TABLE 1-continued
| Entry | R2 |
|---|---|
| 68 | 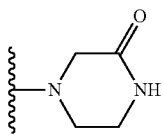 [SMILES: *N1CCNC(=O)C1] |
| 69 | 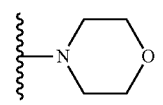 [SMILES: *N1CCOCC1] |
| 70 | 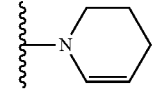 |
| 71 | 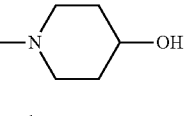 |
| 72 | 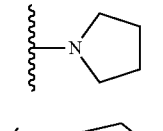 |
| 73 | 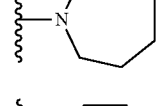 |
| 74 | 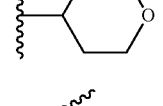 |
| 75 | 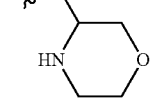 |
| 76 | 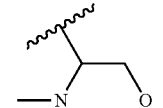 |
| 77 | 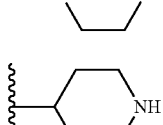 |
| 78 | 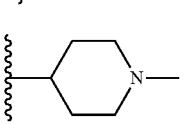 |
| 79 | 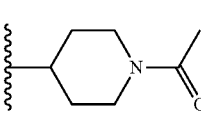 |
| 80 | 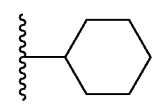 |
| 81 | 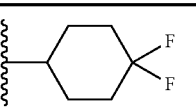 |
| 82 | 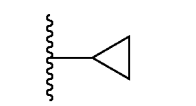 [SMILES: *C1CC1] |
| 83 | 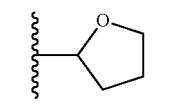 |
| 84 | 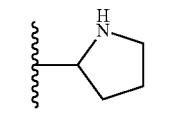 |
| 85 | 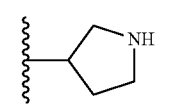 |
| 86 | 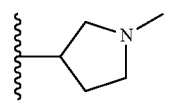 [SMILES: *C1CCN(C)C1] |
| 87 | 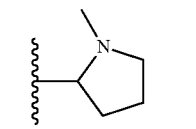 [SMILES: *C1CCCN1C] |
| 88 | 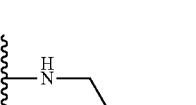 |
| 89 | 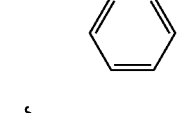 |
| 90 | 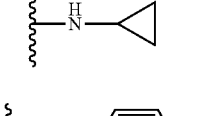 |
| 91 | 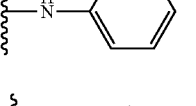 |
| 92 | 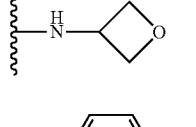 |

TABLE 1-continued
| Entry | R₂ |
|---|---|
| 93 | 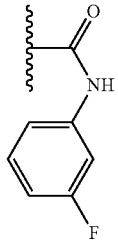 [SMILES: *C(=O)Nc1cccc(F)c1] |
| 94 | 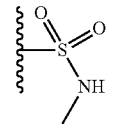 |
| 95 | 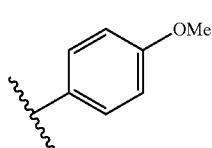 [SMILES: *c1ccc(OC)cc1] |
| 96 | 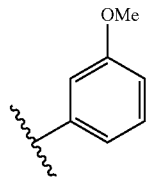 [SMILES: *c1cccc(OC)c1] |
| 97 | 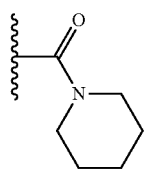 [SMILES: *C(=O)N1CCCCC1] |
| 98 | 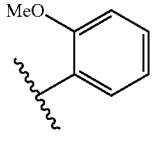 |
| 99 | 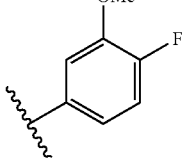 |
| 100 | 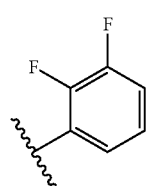 [SMILES: *c1cccc(F)c1F] |
| 101 | 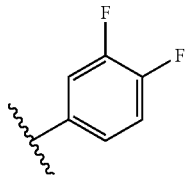 [SMILES: *c1ccc(F)c(F)c1] |
| 102 | 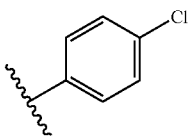 [SMILES: *c1ccc(Cl)cc1] |
| 103 | 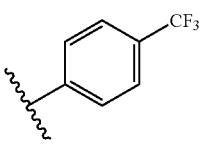 [SMILES: *c1ccc(C(F)(F)F)cc1] |
| 104 | 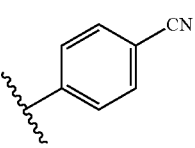 [SMILES: *c1ccc(C#N)cc1] |
| 105 | 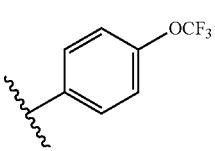 [SMILES: *c1ccc(OC(F)(F)F)cc1] |
| 106 | 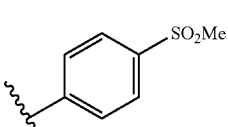 |
| 107 | 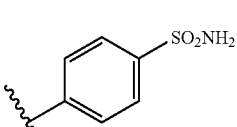 |
| 108 | 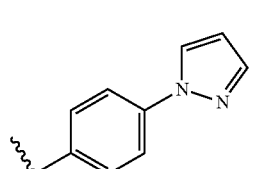 |
| 109 | 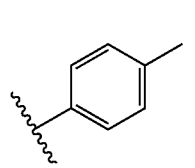 [SMILES: *c1ccc(C)cc1] |

TABLE 1-continued

| Entry | R₂ |
|---|---|
| 110 | 3-methylphenyl |
| 111 | 3-chlorophenyl |
| 112 | 3-(trifluoromethyl)phenyl |
| 113 | 3-cyanophenyl |
| 114 | 3-(trifluoromethoxy)phenyl |
| 115 | 3-(methylsulfonyl)phenyl |
| 116 | 3-isopropoxyphenyl |
| 117 | 3-(2-methoxyethoxy)phenyl |
| 118 | 5-fluoropyridin-2-yl |
| 119 | 5-(trifluoromethyl)pyridin-2-yl |
| 120 | 5-cyanopyridin-2-yl |
| 121 | 5-(methylsulfonyl)pyridin-2-yl |
| 122 | 5-sulfamoylpyridin-2-yl |
| 123 | 5-(trifluoromethoxy)pyridin-2-yl |
| 124 | 5-(dimethylamino)pyridin-2-yl |
| 125 | 6-methylpyridin-2-yl |
| 126 | 6-methoxypyridin-2-yl |

TABLE 1-continued

| Entry | R₂ |
|---|---|
| 127 | 3-fluoro-2-methylpyridin-6-yl |
| 128 | 2-chloro-4-methoxypyridin-6-yl |
| 129 | 3-fluoro-5-methoxypyridin-2-yl |
| 130 | 6-fluoropyridin-3-yl |
| 131 | 6-cyanopyridin-3-yl |
| 132 | 5-methoxypyridin-2-yl |
| 133 | 2-fluoropyridin-4-yl |
| 134 | 2-cyanopyridin-4-yl |
| 135 | 2-methoxypyridin-4-yl |
| 136 | 3-cyano-4-fluorophenyl |
| 137 | 3-fluoro-4-cyanophenyl |
| 138 | 3-methyl-4-cyanophenyl |
| 139 | 1-oxoisoindolin-5-yl |
| 140 | 1H-benzimidazol-6-yl |
| 141 | 3-cyano-1H-indol-6-yl |
| 142 | benzothiazol-6-yl |
| 143 | thieno[2,3-b]pyridin-2-yl |
| 144 | 5-methyl-4,5,6,7-tetrahydrothiazolo[5,4-c]pyridin-2-yl |

TABLE 1-continued
| Entry | R₂ |
|---|---|
| 145 | 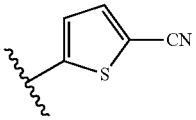 [SMILES: *c1ccc(C#N)s1] |
| 146 | 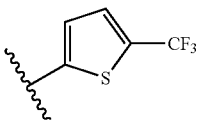 [SMILES: *c1ccc(C(F)(F)F)s1] |
| 147 | 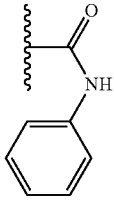 [SMILES: *C(=O)Nc1ccccc1] |
| 148 | 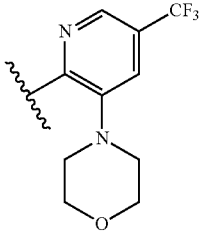 [SMILES: *c1ncc(C(F)(F)F)cc1N1CCOCC1] |
| 149 | 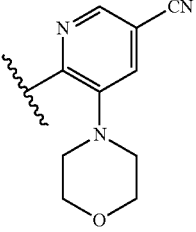 [SMILES: *c1ncc(C#N)cc1N1CCOCC1] |
| 150 | 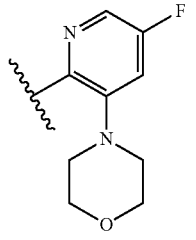 [SMILES: *c1ncc(F)cc1N1CCOCC1] |
| 151 | 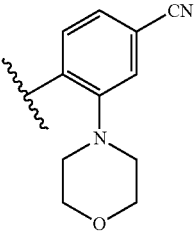 [SMILES: *c1ccc(C#N)cc1N1CCOCC1] |
| 152 | 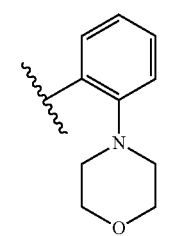 |
| 153 | 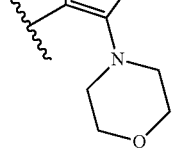 |
| 154 | 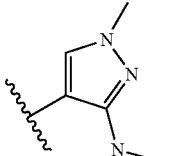 |
| 155 | 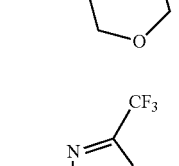 |
| 156 | 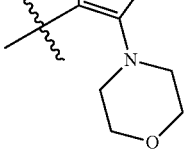 |
| 157 | 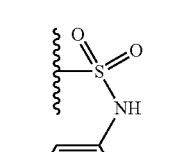 |

TABLE 1-continued
| Entry | R₂ |
|---|---|
| 158 | 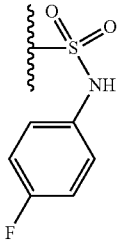 |
| 159 | 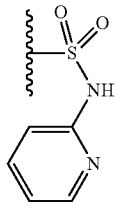 [SMILES: *S(=O)(=O)Nc1ccccn1] |
| 160 | 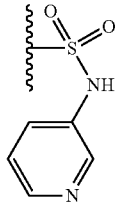 [SMILES: *S(=O)(=O)Nc1cccnc1] |
| 161 | 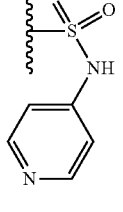 |
| 162 | 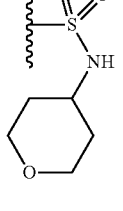 |
| 163 | 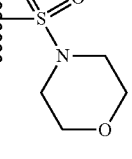 |
| 164 | 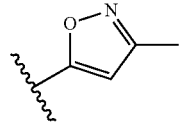 [SMILES: *c1cc(C)no1] |
| 165 | 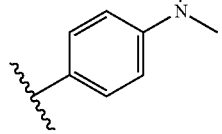 |
| 166 | 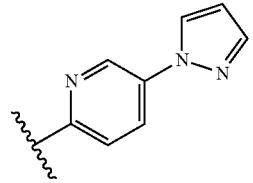 [SMILES: *c1ccc(-n2cccn2)cn1] |
| 167 | 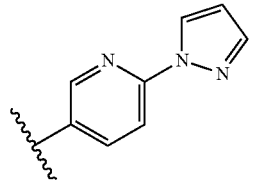 [SMILES: *c1ccc(-n2cccn2)nc1] |
| 168 | 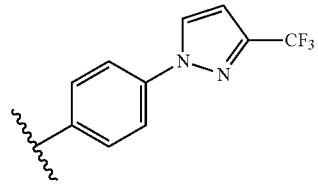 [SMILES: *c1ccc(-n2ccc(C(F)(F)F)n2)cc1] |
| 169 | 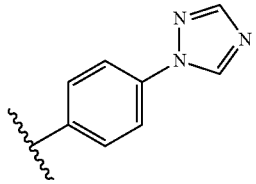 [SMILES: *c1ccc(-n2cncn2)cc1] |
| 170 |  |
| 171 |  |
| 172 |  |

TABLE 1-continued

| Entry | R₂ |
|---|---|
| 173 | 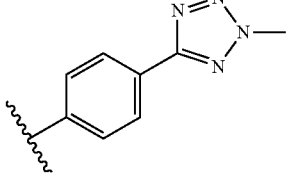 |
| 174 | 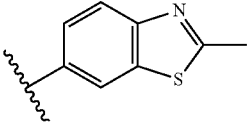 [SMILES: *c1ccc2nc(C)sc2c1] |
| 175 | 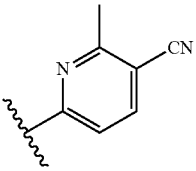 [SMILES: *c1ccc(C#N)c(C)n1] |
| 176 | 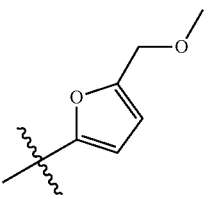 [SMILES: *c1ccc(COC)o1] |
| 177 | 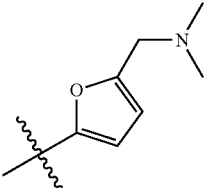 [SMILES: *c1ccc(CN(C)C)o1] |
| 178 |  |
| 179 | 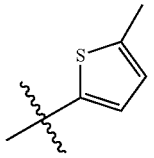 [SMILES: *c1ccc(C)s1] |
| 180 | 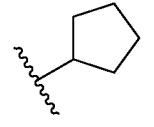 |
| 181 | 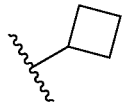 [SMILES: *C1CCC1] |

TABLE 1-continued

| Entry | R₂ |
|---|---|
| 182 | 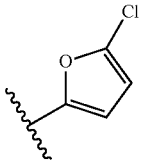 |
| 183 | 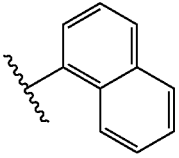 [SMILES: *c1cccc2ccccc12] |
| 184 | 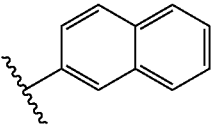 [SMILES: *c1ccc2ccccc2c1] |
| 185 | 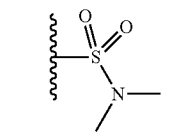 [SMILES: *S(=O)(=O)N(C)C] |
| 186 | 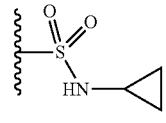 |

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule. For example, wherein in Formula (III-1), each of the two $R_3$ groups may be the same or different.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection is subjects. The method comprises administering a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Preferred heteroaryl groups are monocyclic or bicyclic. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl, and the like. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, bicyclo [2.2.2] octyl, spiro[2.5] octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1] non-3-en-9-yl, and the like.

As used herein, the term "arylalkyl" means a functional group wherein an alkylene chain is attached to an aryl group, e.g., benzyl, —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. Examples include, but are not limited to, pyridinylmethyl, pyrimidinylethyl and the like. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, OC(O)$NH_2$, $S(O)_2NH$, $S(O)_2NH_2$, $NHC(O)NH_2$, NHC(O) C(O)NH, $NHS(O)_2NH$, $NHS(O)_2NH_2$, C(O)$NHS(O)_2$, C(O)$NHS(O)_2NH$ or C(O)$NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —C$_1$, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —NO$_2$, —N$_3$, —CN, —NH$_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —CONH$_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —OCO$_2$—$C_1$-$C_{12}$-alkyl, —OCO$_2$—$C_2$-$C_8$-alkenyl, —OCO$_2$—$C_2$-$C_8$-alkynyl, —OCO$_2$—$C_3$-$C_{12}$-cycloalkyl, —OCO$_2$-aryl, —OCO$_2$-heteroaryl, —OCO$_2$-heterocycloalkyl, —CO$_2$—$C_1$-$C_{12}$ alkyl, —CO$_2$—$C_2$-$C_8$ alkenyl, —CO$_2$—$C_2$-$C_8$ alkynyl, —CO$_2$—$C_3$-$C_{12}$-cycloalkyl, —CO$_2$-aryl, CO$_2$-heteroaryl, CO$_2$-heterocyloalkyl, —OCONH$_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —NHCO$_2$—$C_1$-$C_{12}$-alkyl, —NHCO$_2$—$C_2$-$C_8$-alkenyl, —NHCO$_2$—$C_2$-$C_8$-alkynyl, —NHCO$_2$—$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —SO$_2$NH$_2$, —SO$_2$NH—$C_1$-$C_{12}$-alkyl, —SO$_2$NH—$C_2$-$C_8$-alkenyl, —SO$_2$NH—$C_2$-$C_8$-alkynyl, —SO$_2$NH—$C_3$-$C_{12}$-cycloalkyl, —SO$_2$NH-aryl, —SO$_2$NH-heteroaryl, —SO$_2$NH-heterocycloalkyl, —NHSO$_2$—$C_1$-$C_{12}$-alkyl, —NHSO$_2$—$C_2$-$C_8$-alkenyl, —NHSO$_2$—$C_2$-$C_8$-alkynyl, —NHSO$_2$—$C_3$-$C_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," or "protogenic organic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BTC for bis(trichloromethyl)carbonate; triphosgene;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-;
1-O-(2-cyanoethyl)-(N,N-diisopropyl)-phosphoramidite;
DBU for 1,8-Diazabicycloundec-7-ene;
DCC for N,N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DSC for N, N'-disuccinimidyl carbonate;
DUPHOS for

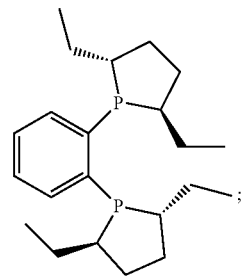 [SMILES: CC[C@@H]1CC[C@@H](CC)P1c1ccccc1P1[C@H](CC)CC[C@H]1CC ; ";"]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for 0 (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;

Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethyl amine;
Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or PPh$_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene; and
Zhan 1 B for

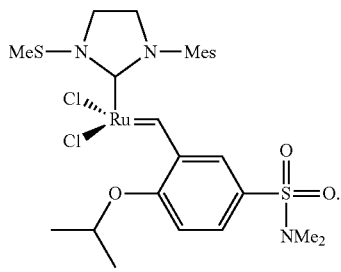

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel RSV analogs of the compounds of formula 10 or 11 or 12 are prepared starting from compounds 1, 2, and 3. A procedure similar to that described by Sherrill and Sugg (*J. Org. Chem.* 1995, 60, 730-734) was followed to get to the intermediate having the formula 8. Firstly, 1, 2, and 3 are heated in an appropriate solvent like, but not limited to, toluene to form compound 4. Compound 4 is converted to the corresponding acid chloride, using the appropriate conditions, and is then reacted with 5, wherein R$_1$ and R$_3$ are as previously defined and at least one X is a nitrogen atom, to form compound 6. Compound 6 is reacted with ammonia, followed by reaction with ammonium acetate in acetic acid to form compound 7. The Cbz group in 7 is removed using HBr in acetic acid to afford the intermediate amine 8. Compound 8 is a common intermediate that can be used in various ways to access compounds of the formula (10-12). Compound 8 is reacted with thiocarbonyldiimidazole (TCDI) to generate an intermediate urea that is reacted further with hydrazine to afford the semicarbazide 9. Compound 9 is reacted with a variety of carboxylic acids using EDCI/HOBt, or a suitable coupling reagent, followed by heating to give the desired 1,3,4-aminooxadiazole compounds 10 as a racemic mixture. The racemic mixture of 10 can be separated into the individual pure enantiomers 11 and 12 using chiral chromatography.

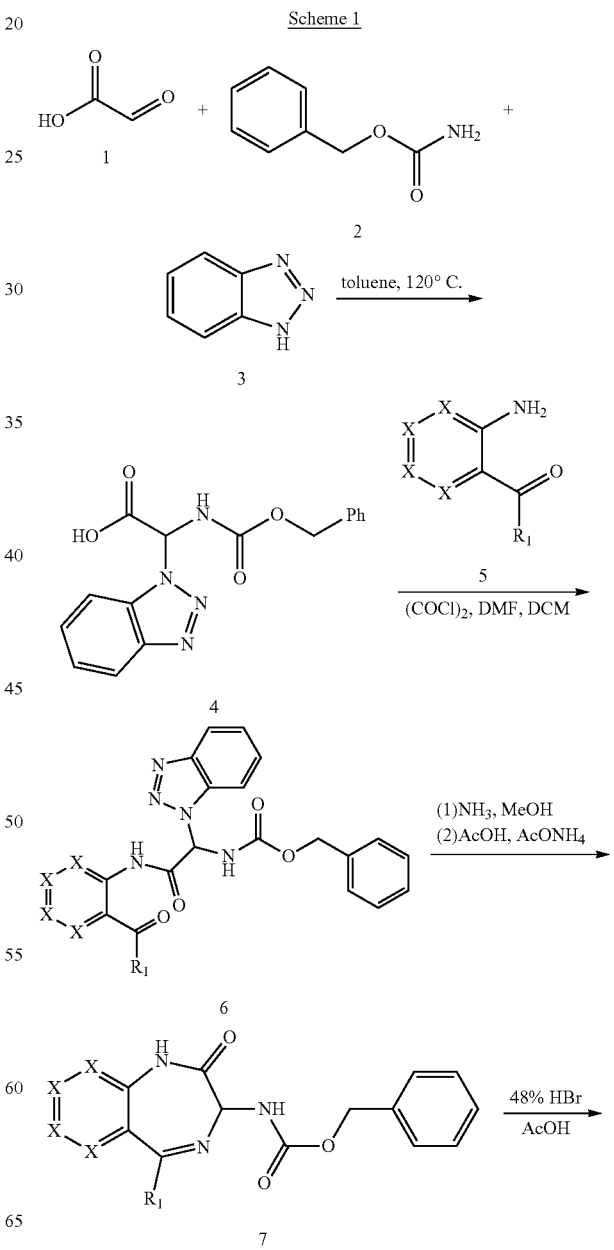

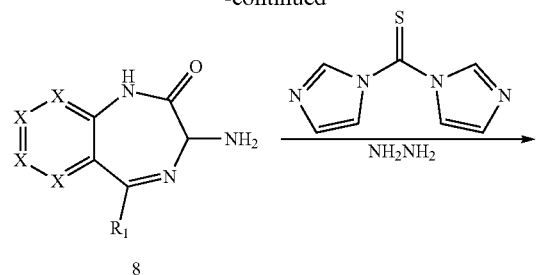

8

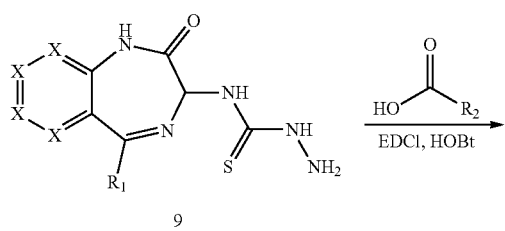

9

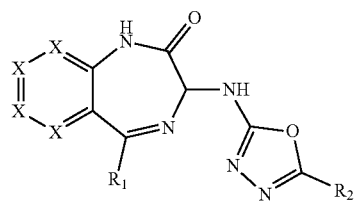

10

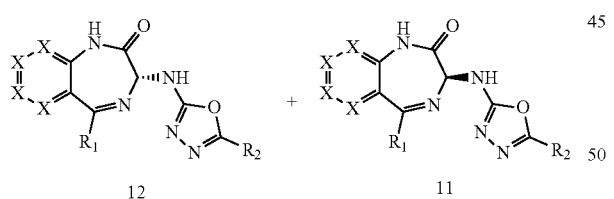

12 + 11

At least one X is N and the remaining Xs are N or CR$_{15}$
R$_{15}$ is H or R$_3$ Scheme 2 follows a similar scheme to that described for scheme 1 except that the acid chloride generated from intermediate 4 is reacted with a 5-membered heteroaryl 13 instead of a 6-membered nitrogen heteroaryl 5 to give the intermediate 14, wherein one Y is O, S or NR$_{15}$ and the other two Ys are independently N or CR$_{15}$, wherein R$_{15}$ is hydrogen or R$_3$. Compound 14 is carried through the same reaction path described in scheme 1 to afford the racemic target compounds 18 that can be purified into the corresponding pure enantiomers 19 and 20 via column chromatography.

Scheme 2

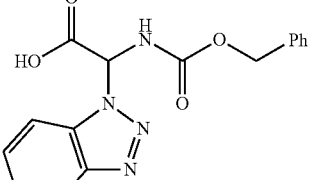

13

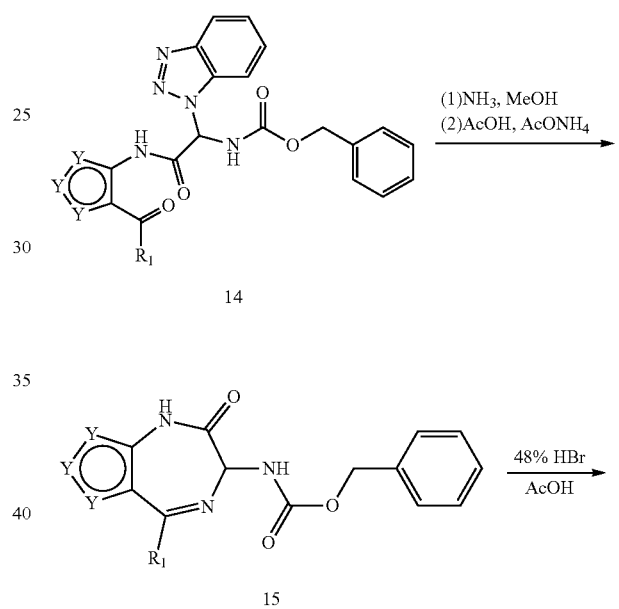

14

15

16

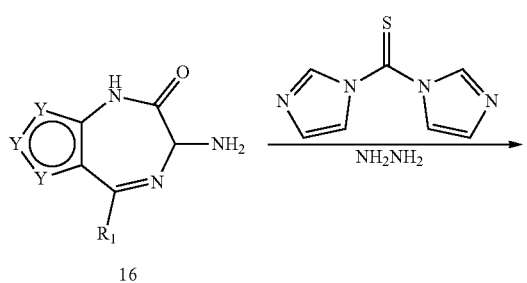

17

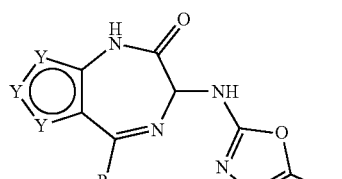

18

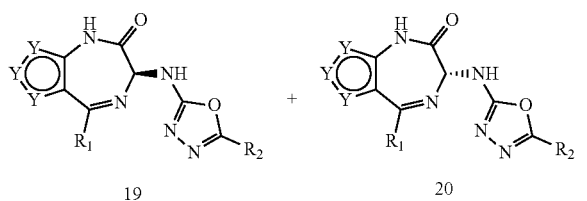

19       20 one Y is O, S or NR$_{15}$ the other two Ys are independently N or CR$_{15}$
R$_{15}$ is hydrogen or R$_3$ Scheme 3 illustrates methods, wherein R$_1$, R$_2$, and R$_3$ are defined as previously described, to prepare compounds of formulas 21 and 22. Following Path 1 amine 8 is reacted with TCDI and hydrazine to generate the intermediate 9. Intermediate 9 can be coupled with carboxylica acids to form the intermediate 21. Compounds 21 can be reacted with tosyl chloride (TsCl) to afford the thiadiazoles of formula 22. Amine 16 can be carried through an analogous sequence of reactions to afford target compounds 23. Both 22 and 23 can be separated into the corresponding enantiomers using chiral chromatography.

Scheme 3

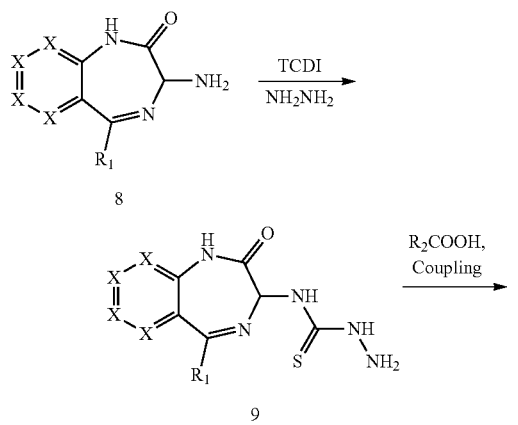

8

At least one X is N and the remaining Xs are N or CR$_{15}$
R$_{15}$ is H or R$_3$

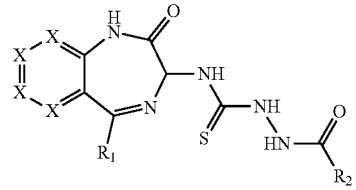

21

TsCl, TEA, NMP

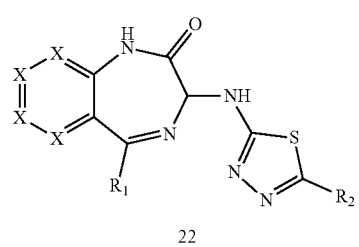

22

16       23 one Y is O, S or NR$_{15}$
the other two Ys are independently N or CR$_{15}$
R$_{15}$ is hydrogen or R$_3$ Scheme 4 illustrates methods, wherein R$_1$, R$_2$, and R$_3$ are defined as previously described, to prepare compounds of formula 25 and 26. Amine 8 is reacted with TCDI to generate the intermediate 24 that is reacted with alpha-azido ketones to generate the oxazole 25. Amine 16 can be carried through an analogous sequence of reactions to afford target compounds 26. Both 25 and 26 can be separated into the corresponding enantiomers using chiral chromatography.

Scheme 4

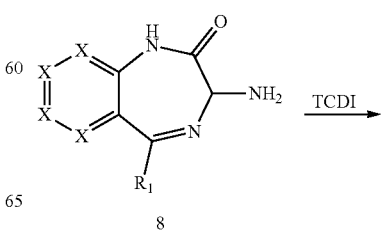

8

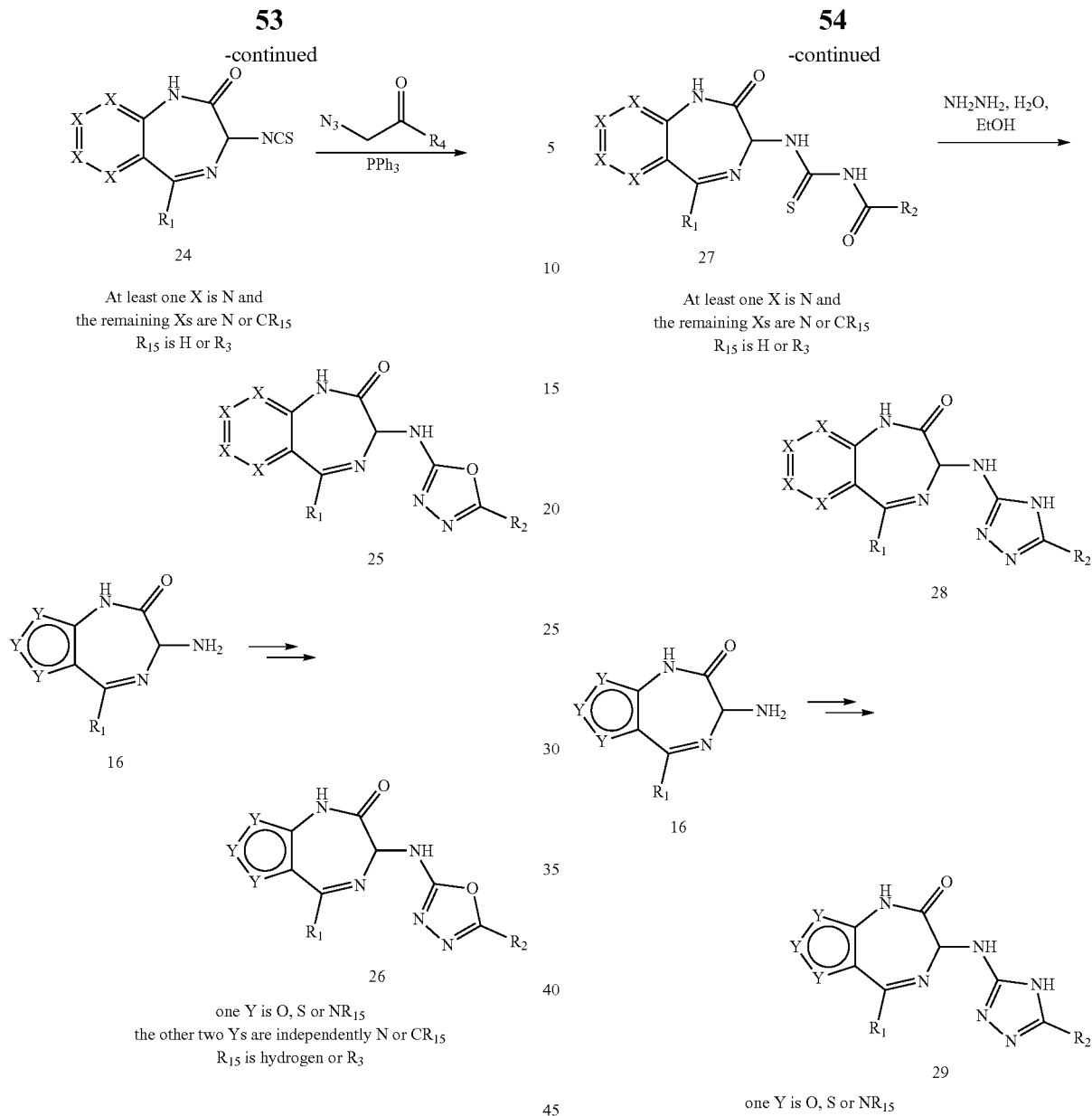

Scheme 5 illustrates methods, wherein $R_1$, $R_2$, and $R_3$ are defined as previously described, to prepare compounds of formula 28 and 29. Amine 8 is reacted with isothiocyanates to give the intermediate 27 that is reacted further with hydrazine to give triazoles having the formula 28. Amine 16 can be carried through an analogous sequence of reactions to afford target compounds 29. Both 28 and 29 can be separated into the corresponding enantiomers using chiral chromatography.

Scheme 5

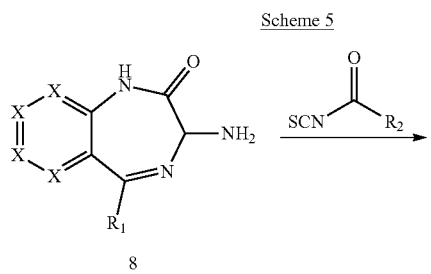

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims. Unless otherwise indicated, each of the compounds of the examples below was prepared and tested as a racemic mixture or, when possible, a diastereomeric mixture.

Example 1

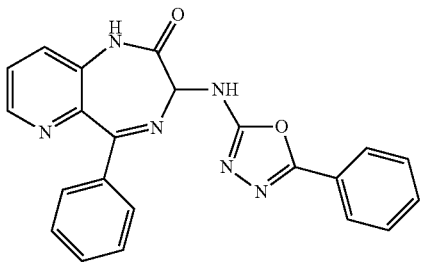 [SMILES: O=C1Nc2cccnc2C(c2ccccc2)=NC1Nc1nnc(-c2ccccc2)o1]

Example 1 Step a

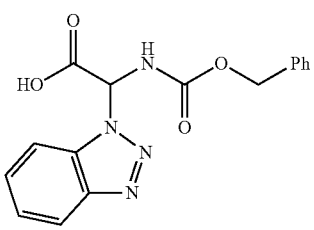 [SMILES: O=C(NC(C(=O)O)n1nnc2ccccc21)OCc1ccccc1]

To a 250 mL flask equipped mechanical stirring, was added 2-oxoacetic acid hydrate (9.2 g, 0.1 mol), benzyl carbamate (15.1 g, 0.1 mol) and 1H-benzo[d][1,2,3]triazole (9.2 g, 0.1 mol), and toluene (300 mL). The resulting solution was stirred for 2 h at 120° C. in an oil bath. The resulting mixture was filtered and the solid residue was washed with petroleum ether (3×), and dried in vacuo to give 2-(1H-benzo[d][1,2,3]triazol-1-yl)-2-(benzyloxycarbonylamino)acetic acid (28.6 g, 87%) as a white solid that was used without further purification. ESI-MS m/z: 327 [M+H]⁺.

Example 1 Step b

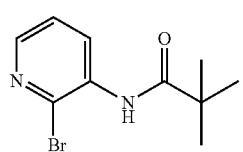

A solution of the pivaloyl chloride (7.2 g, 60 mmol) was added dropwise to 2-bromopyridin-3-amine (8.6 g, 50 mmol) and TEA (7.6 g, 75 mmol) in DCM (150 mL) at 0° C. The mixture was stirred for 1 h at rt. Then H₂O (100 mL) was added to the mixture and extracted with EA (3×). The organic layer was dried and purified by reverse phase C18 column chromatography (MeCN:H₂O) to give desired compound as light brown oil (11.5 g, 90%). ESI-MS m/z: 256.9 [M+H]⁺.

Example 1 Step c

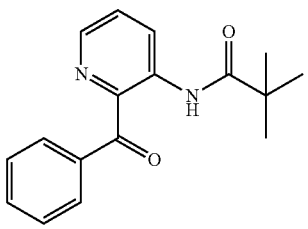 [SMILES: CC(C)(C)C(=O)Nc1cccnc1C(=O)c1ccccc1]

ⁿBuLi (20 mL, 50 mmol) was added dropwise to the compound from step b (5.12 g, 20 mmol) in THF (100 mL) at −78° C. and stirred for 1 h. Then N-methoxy-N-methyl-benzamide (4.95 g, 30 mmol) in THF (30 mL) was added dropwise to the mixture at −78° C. and stirred at rt for 2 hours. The mixture was quenched with H₂O (100 mL) and extracted with EA (×3). The organic layer was combined, dried over Na₂SO₄ and concentrated to afford the crude product as a brown oil (2.8 g, 50%). ESI-MS m/z: 283.0 [M+H]⁺.

Example 1 Step d

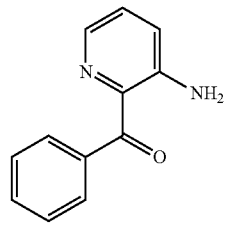 [SMILES: Nc1cccnc1C(=O)c1ccccc1]

A solution of the compound from step c (2.8 g, 10 mmol) was dissolved in HCl (5N, 120 mL) and MeOH (30 ml). The mixture was stirred for 36 h at 100° C. it was adjusted PH to 8 and extracted with EA (×3), The organic layer was combined, dried over Na₂SO₄, concentrated and purified by reverse phase C18 column chromatography (MeCN:H₂O) to give the desired compound as a yellow solid (1.6 g, 80%). ESI-MS m/z: 199.0 [M+H]⁺.

Example 1 Step e

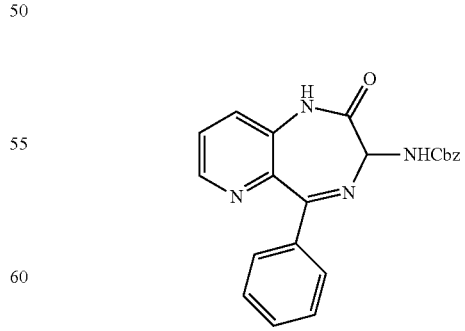

Oxalyl dichloride (1.27 g, 10 mmol) was added dropwise to acid from step a (3.26 g, 10 mmol) and DMF (0.5 mL) in THF (50 mL) at 0° C. and stirred for 1 h. Then the compound from step d (1.58 g, 8 mmol) and NM (2.02 g, 20 mmol) was added dropwise to the mixture and stirred for 0.5 h at rt. Solid was filtered out and the filtrate was concentrated. NH$_3$ in MeOH (7 N, 50 mL) was added to the mixture and stirred for 2 h. Then it was extracted with EA (×3) and washed with NaOH (1 N, 100 mL), the organic layer was combined, concentrated. The residue was dissolved in AcOH (50 mL), NH$_4$OAc (3.85 g, 40 mmol) was added and it was stirred at rt for 18 h. then it was adjusted PH to 9. Solid was collected and washed with Et$_2$O (50 mL) to give desired compound as a yellow solid (1.93 g, 63%). ESI-MS m/z: 387.1 [M+H]$^+$.

Example 1 Step f

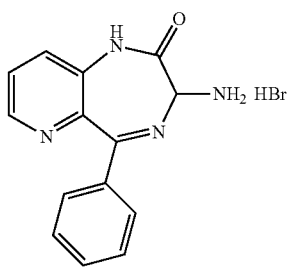 [SMILES: NC1N=C(c2ccccc2)c2ncccc2NC1=O ; Br]

A solution of the compound from step e (772 mg, 2 mmol) was dissolved in HBr/AcOH (5 mL) and stirred at 70° C. for 0.5 h. Then the mixture was cooled to 0° C. and Et$_2$O (30 mL) was added. Solid was collected to give the product as a grey solid (302 mg, 60%). ESI-MS m/z: 253.0 [M+H]$^+$.

Example 1 Step g

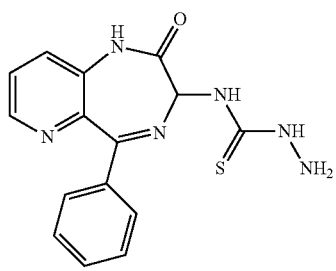 [SMILES: NNC(=S)NC1N=C(c2ccccc2)c2ncccc2NC1=O]

A solution of the compound from step f (101 mg, 0.4 mmol) was added to di(1H-imidazol-1-yl)methanethione (101 mg, 0.6 mmol) in DMF (5 mL) and stirred at rt for 1 h. Then NH$_2$NH$_2$ (2 mL) was added to the mixture and stirred for 1 h. It was poured into water and extracted with EA (×3). The organic layer was concentrated to give the title compound as a grey solid (98 mg, 75%). ESI-MS m/z: 327.0 [M+H]$^+$.

Example 1 Step h

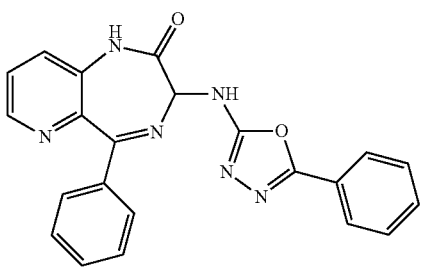 [SMILES: O=C1Nc2cccnc2C(c2ccccc2)=NC1Nc1nnc(-c2ccccc2)o1]

A solution of the compound from step g (98 mg, 0.3 mmol) was added to benzoic acid (73.2 mg, 0.6 mmol), EDCI (287 mg, 1.5 mmol) and HOBt (81 mg, 0.6 mmol) in DMF (5 mL) and stirred at rt for 1 h. Then the mixture was stirred at 60° C. for 2 h. The mixture was purified by prep-HPLC to give the title compound as a light yellow solid (36 mg, 31%). $^1$H NMR (300 MHz, DMSO-d$_6$) δ 5.33 (d, J=8.4 Hz, 1H), 7.36-7.92 (m, 12H), 8.56 (dd, J=4.3, 1.6 Hz, 1H), 9.16 (d, J=8.4 Hz, 1H), 11.15 (s, 1H). ESI-MS m/z: 397.1 [M+H]$^+$.

Example 2

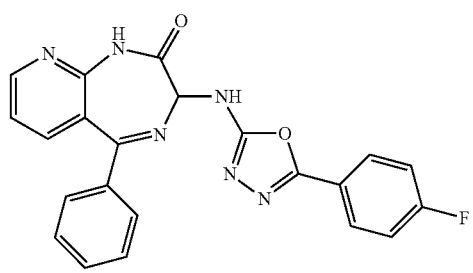 [SMILES: O=C1Nc2ncccc2C(c2ccccc2)=NC1Nc1nnc(-c2ccc(F)cc2)o1]

Example 2 was prepared using a procedure similar to that used to prepare Example 1 where 3-bromopyridin-2-amine and 4-fluorobenzoic acid were used in place of 2-bromopyridin-3-amine and benzoic acid, respectively. ESI-MS m/z: 415.2 [M+H]$^+$. $^1$H NMR (300 MHz, DMSO-d$_6$) δ 5.20 (d, J=8.4 Hz, 1H), 7.26-7.67 (m, 8H), 7.77-7.94 (m, 3H), 8.45 (s, 0.2H), 8.71 (m, 1H), 9.20 (d, J=8.4 Hz, 1H), 11.47 (s, 1H).

Example 3

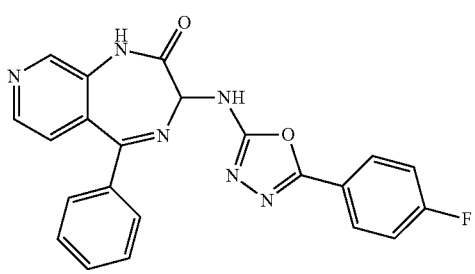 [SMILES: O=C1Nc2cnccc2C(c2ccccc2)=NC1Nc1nnc(-c2ccc(F)cc2)o1]

Example 3 was prepared using a procedure similar to that used to prepare Example 1 where 4-bromopyridin-3-amine and 4-fluorobenzoic acid were used in place of 2-bromopyridin-3-amine and benzoic acid, respectively. ESI-MS m/z: 415.3 [M+H]$^+$. $^1$H NMR (300 MHz, DMSO-d$_6$) δ 5.21 (d, J=8.3 Hz, 1H), 7.31 (d, J=5.2 Hz, 1H), 7.34-7.60 (m, 8H), 7.82-7.93 (m, 2H), 8.43 (d, J=5.1 Hz, 1H), 8.66 (s, 1H), 9.17 (d, J=8.5 Hz, 1H), 11.28 (s, 1H).

Example 4

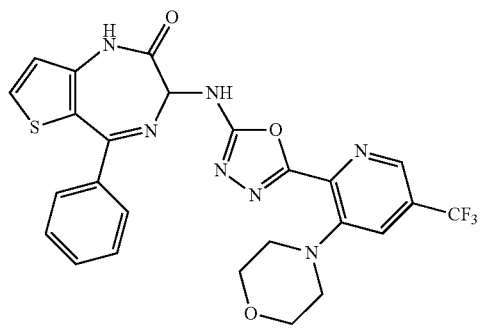 [SMILES: O=C1Nc2ccsc2C(c2ccccc2)=NC1Nc1nnc(-c2ncc(C(F)(F)F)cc2N2CCOCC2)o1]

Example 4 Step a

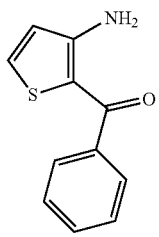 [SMILES: Nc1ccsc1C(=O)c1ccccc1]

Phenylmagnesium bromide (9.7 mL, 29.0 mmol) was dropwised to the solution of 3-aminothiophene-2-carbonitrile (900 mg, 7.3 mol) in THF (10 mL) at 0° C. The mixture was stirred for 4 hours at 70° C. in an oil bath. The mixture was cooled to 0° C. and HCl (5 mL, 1 M) was added. The mixture was stirred for 1 hour at 70° C. in an oil bath. The mixture was concentrated and to the mixture was added water and extracted with EA (×3). The organic layer was dried and concentrated. The residue was purified by reverse phase C18 column chromatography (MeCN:H$_2$O) to give desired compound as an orange solid (370 mg, 25%). ESI-MS m/z: 204.1 [M+H]$^+$.

Example 4 Step b

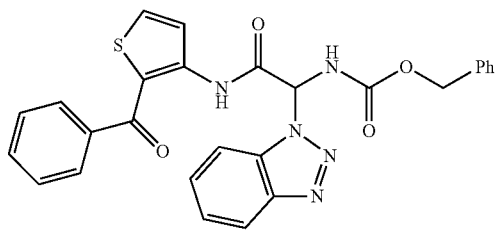 [SMILES: O=C(NC(C(=O)Nc1ccsc1C(=O)c1ccccc1)n1nnc2ccccc21)OCc1ccccc1]

A solution of oxalic dichloride (1.17 g, 9.0 mmol) in THF (5 mL) was dropwised to the solution of the acid from Example 1 step a (3 g, 9.0 mmol) in THF (10 mL) at 0° C. then DMF (0.2 mL) was added. The mixture was stirred for 1 hour at 0° C. in a water/ice bath. To the mixture was added the compound from step a (370 mg, 1.8 mmol), PPY (540 mg, 3.6 mmol) in THF (5 mL) and stirred for an additional 0.5 hours at rt. The mixture was quenched with water, concentrated. The residue was purified by reverse phase C18 column chromatography (MeCN:H$_2$O) to give desired compound as a yellow solid (760 mg, 82%). ESI-MS m/z: 534.5 [M+H]$^+$.

Example 4 Step c

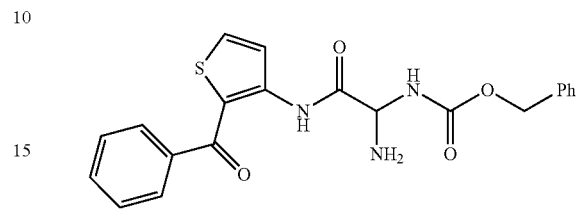

A solution of the compound from step b (750 mg, 1.47 mmol) in MeOH (5 mL) and ammonia (5 mL) was stirred for 1 hour at rt. The mixture was diluted with water, extracted with EA (×3), the organic layer was dried, concentrated to give 640 mg (crude) of desired compound as orange solid, which was used directly in the next step. ESI-MS m/z: 432.2 [M+H]$^+$.

Example 4 Step d

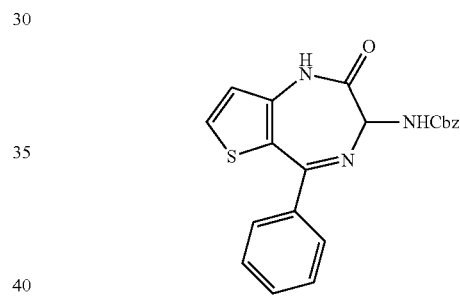

A solution of the compound from step c (640 mg, 1.57 mmol) and CH$_3$COONH$_4$ (723 mg, 9.39 mmol) in acetic acid (10 mL) was stirred for 72 hours at rt. The mixture was concentrated, NaOH (1 M) was used to adjust the pH to 10. The mixture was extracted with EA (×3), the organic layer was dried, concentrated. The crude product was purified by reverse phase C18 column chromatography (MeCN:H$_2$O) to give desired compound as light yellow solid (248 mg, 41%). ESI-MS m/z: 392.1 [M+H]$^+$.

Example 4 Step e

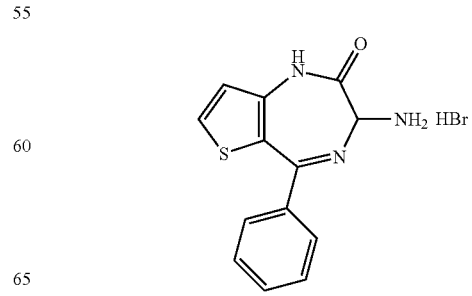

A solution of the compound from step d (248 mg, 0.63 mmol) in HBr/HOAc (5 mL) was stirred for 15 minutes at 70° C. in an oil bath. The mixture was diluted with ether (100 mL). The solid was collected by filtration to give 210 mg (crude) of desired compound as yellow solid, which was used directly in the next step. ESI-MS m/z: 258.2 [M+H]⁺.

Example 4 Step f

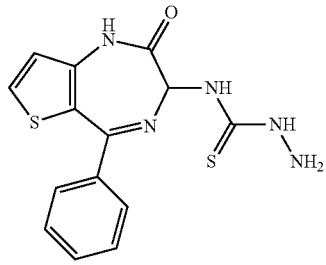 [SMILES: NNC(=S)NC1N=C(c2ccccc2)c2sccc2NC1=O]

TEA (0.5 mL) was added to the solution of the compound from step e (180 mg, 0.53 mmol) in DMF (3 mL) at 0° C. TCDI (190 mg, 1.07 mmol) was added at 0° C. and the mixture was stirred for 40 minutes at 0° C. in water/ice bath. NH₂NH₂.H₂O (0.5 mL) was added and the mixture was stirred for 20 minutes at rt. The mixture was purified by reverse phase C18 column chromatography (MeCN:H₂O) to give desired compound as yellow solid (130 mg, 74%). ESI-MS m/z: 332.0 [M+H]⁺.

Example 4 Step g

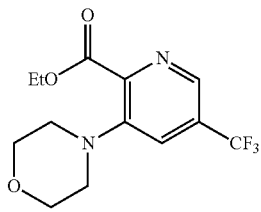 [SMILES: CCOC(=O)c1ncc(C(F)(F)F)cc1N1CCOCC1]

A solution of the ethyl 3-chloro-5-(trifluoromethyl)picolinate (190 g, 0.75 mol) in morpholine (neat) (500 mL) was stirred for 4 hrs at 100° C. The reaction mixture was cooled to rt and diluted with water (800 mL). Then it was extracted with EtOAc (3×). The organic phase was washed with brine and water and dried over Na₂SO₄, then solvent was removed to afford crude product (240 g), which was used directly in next step. ESI-MS m/z: 305.2 [M+H]⁺.

Example 4 Step h

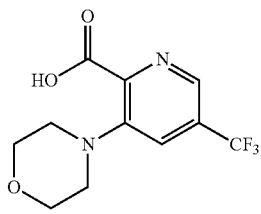 [SMILES: O=C(O)c1ncc(C(F)(F)F)cc1N1CCOCC1]

A solution of the compound from step g (1.49 g, 5.0 mol) and LiOH.H₂O (2.06 g, 50.0 mol) in THF (5 mL) and H₂O (5 mL) was stirred for 1 hour. The mixture was purified by reverse phase C18 column chromatography (MeCN:H₂O) to give 3-morpholino-5-(trifluoromethyl)picolinic acid as yellow solid (800 mg, 58%). ESI-MS m/z: 277.2 [M+H]⁺.

Example 4 Step i

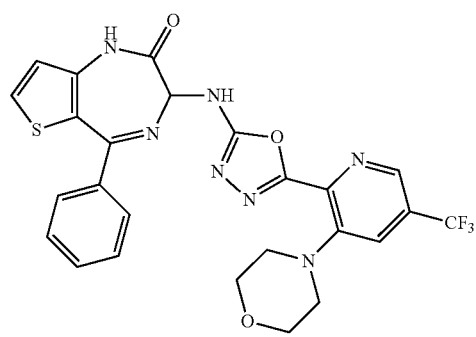 [SMILES: O=C1Nc2ccsc2C(c2ccccc2)=NC1Nc1nnc(-c2ncc(C(F)(F)F)cc2N2CCOCC2)o1]

A solution of the compound from step f (130 mg, 0.39 mmol), the compound from step h (130 mg, 0.47 mmol), EDCI (300 mg, 1.57 mmol) and HOBt (80 mg, 0.59 mmol) in DMF (3 mL) was stirred for 2 hours at rt and then 2 hours at 60° C. in an oil bath. The crude product was purified by Prep-HPLC (MeCN/H₂O) to give the title compound as a yellow solid (39 mg, 18%). ESI-MS m/z: 556.4 [M+H]⁺. ¹H NMR (300 MHz, DMSO-d₆) δ 3.08 (m, 4H), 3.74 (m, 4H), 5.25 (d, J=8.4 Hz, 1H), 7.05 (d, J=5.3 Hz, 1H), 7.52 (m, 3H), 7.68 (m, 2H), 7.89 (d, J=1.8 Hz, 1H), 8.03 (d, J=5.2 Hz, 1H), 8.69 (s, 1H), 9.39 (d, J=8.3 Hz, 1H), 11.43 (s, 1H).

Example 5

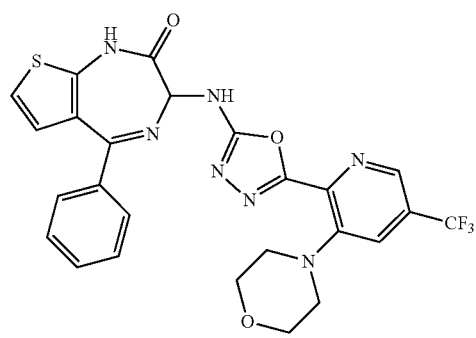 [SMILES: O=C1Nc2sccc2C(c2ccccc2)=NC1Nc1nnc(-c2ncc(C(F)(F)F)cc2N2CCOCC2)o1]

Example 5 Step a

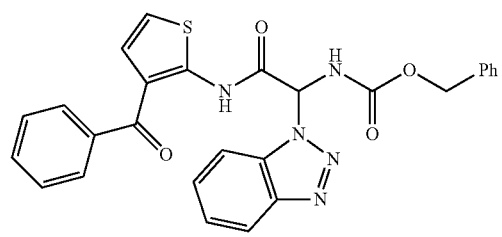 [SMILES: O=C(NC(C(=O)Nc1sccc1C(=O)c1ccccc1)n1nnc2ccccc21)OCc1ccccc1]

A solution of oxalic dichloride (1.27 g, 0.01 mol) in THF (10 mL) was added dropwise to the solution of the compound from Example 1 step a (3.26 g, 0.01 mol) in THF (20 mL) at 0° C. before DMF (0.1 mL) was added. It was stirred for 0.5 hour at 0° C. in a water/ice bath. To the mixture was added (2-aminothiophen-3-yl) (phenyl)methanone (1 g, 5 mmol), PPY (2.22 g, 0.015 mol) in THF (10 mL) and stirred for an additional 0.5 hour at rt. It was quenched with water, concentrated. The residue was purified by reverse phase C18 column chromatography (MeCN:H₂O) to give desired compound as a yellow solid (2.4 g, 94%). ESI-MS m/z: 534.4 [M+H]⁺.

Example 5 Step b

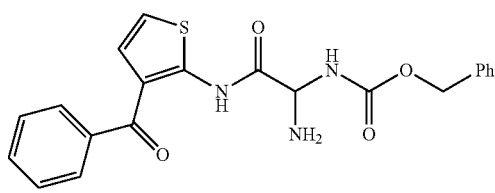 [SMILES: NC(NC(=O)OCc1ccccc1)C(=O)Nc1sccc1C(=O)c1ccccc1]

A solution of the compound from step a (1.4 g, 2.7 mmol) in MeOH (10 mL) and ammonia (1 mL) was stirred for 30 minutes at 0° C. It was diluted with water, extracted with EA (×3). The organic layer was dried, concentrated to give 883 mg (crude) of desired compound as orange oil, which was used directly in the next step. ESI-MS m/z: 432.1 [M+H]⁺.

Example 5 Step c

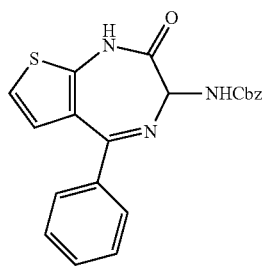 [SMILES: O=C(NC1N=C(c2ccccc2)c2ccsc2NC1=O)OCc1ccccc1]

A solution of the compound from step b (883 mg, 2.16 mmol) and CH₃COONH₄ (998 mg, 12.96 mmol) in acetic acid (5 mL) was stirred for 48 hours at rt. It was concentrated, and NaOH (1 M) was used to adjust the pH to 10, extracted with EA (×3). The organic layer was dried and concentrated. The crude product was purified by reverse phase C18 column chromatography (MeCN:H₂O) to give desired compound as orange oil (260 mg, 31%). ESI-MS m/z: 392.2 [M+H]⁺.

Example 5 Step d

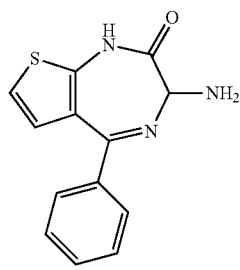 [SMILES: NC1N=C(c2ccccc2)c2ccsc2NC1=O]

A solution of the compound from step c (260 mg, 0.67 mmol) in HBr/HOAc (10 mL) was stirred for 30 minutes at 70° C. in an oil bath. It was diluted with ether (100 mL). The solid was collected by filtration, and ammonium hydroxide was employed to adjust the pH to 8. The solution was freeze-drying to give 200 mg (crude) of desired compound as yellow solid, which was used directly in the next step. ESI-MS m/z: 285.1 [M+H]⁺.

Example 5 Step e

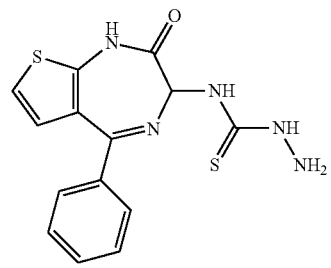 [SMILES: NNC(=S)NC1N=C(c2ccccc2)c2ccsc2NC1=O]

A solution of the compound from step d (257 mg, 1.0 mmol), TCDI (178 mg, 1.0 mmol) in DMF (5 mL) was stirred for 30 minutes at 0° C. Then hydrazine hydrate (1 mL) was added and it was stirred for another 30 minutes. Then H₂O (20 mL) was added to the mixture and extracted with EA (×3). The organic layer was dried and purified by reverse phase C18 column chromatography (MeCN:H₂O) to give desire compound as yellow solid (30 mg, 9%). ESI-MS m/z: 332.1 [M+H]⁺.

Example 5 Step f

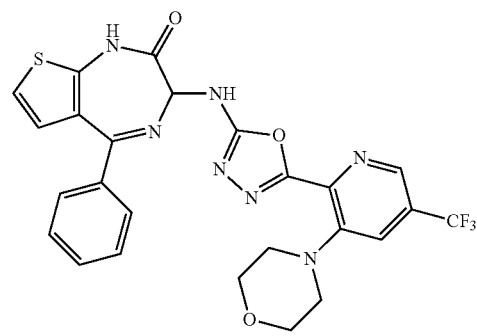 [SMILES: O=C1Nc2sccc2C(c2ccccc2)=NC1Nc1nnc(-c2ncc(C(F)(F)F)cc2N2CCOCC2)o1]

A solution of the compound from step e (15 mg, 0.04 mmol), 3-morpholino-5-(trifluoromethyl)picolinic acid from Example 4 step h (19 mg, 0.06 mmol), EDCI (35 mg, 0.18 mmol), HOBt (9 mg, 0.06 mmol) in DMF (3 mL) was stirred at rt overnight and then at 60° C. for 1 hour. Then H₂O (20 mL) was added to the mixture and extracted with EA (×3). The organic layer was dried and purified by reverse phase C18 column chromatography (MeCN:H₂O) to give desire compound as an off-white solid (7 mg, 30%). ESI-MS m/z: 556.2 [M+H]⁺. ¹H NMR (400 MHz, DMSO-d₆) δ 3.07-3.09 (m, 4H), 3.73-3.75 (m, 4H), 5.27-5.29 (d, 1H), 6.92-6.94 (m, 1H), 7.32-7.33 (m, 4H), 7.46-7.54 (m, 3H), 7.55-7.60 (m, 2H), 7.62-7.89 (m, 1H), 8.69 (s, 1H), 9.38-9.40 (d, J=8.0, 1H), 11.75 (s, 1H).

Examples 6 and 7

Example 6

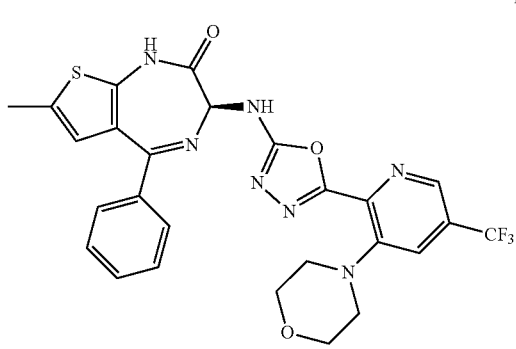

Example 7

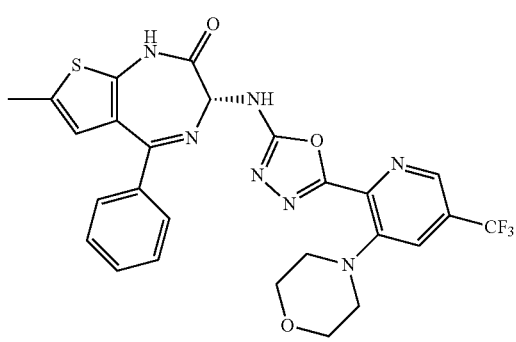

Examples 6 and 7 Step a

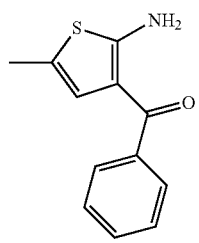

The compound 1 (8.0 g, 55.1 mmol) was dissolved in EtOH (80 mL). Sulfur (3.5 g, 110.2 mmol) and Et₃N (11.2 g, 110.2 mmol) was added. The mixture was heated to 40° C. and a solution of propionaldehyde (6.4 g, 110.2 mmol) in EtOH (30 mL) was added. The mixture was heated to 60° C. for 3 hours and then concentrated. Water (200 mL) was added and the mixture was extracted with EA (200 mL×3). The combined organic phase was dried over anhydrous Na₂SO₄ and concentrated. The residue was purified by silica gel chromatography (PE:EA=10:1) to give the desired product as a yellow solid (8.4 g, 70%). ESI-MS m/z: 217.9 [M+H]⁺.

Examples 6 and 7 Step b

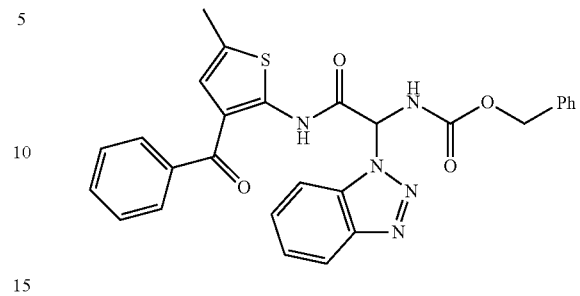

The acid from Example 1 step a (3.6 g, 11.0 mmol) was dissolved in THF (100 mL) and cooled with ice bath. Oxalyl dichloride (1.2 g, 9.2 mmol) was added and then DMF (0.1 mL) was added. The mixture was stirred at this temperature for 30 minutes. A solution of the compound from step a (2.0 g, 9.2 mmol) and PPY (2.73 g, 18.4 mmol) in DCM (20 mL) was added. The mixture was warmed to rt and stirred for 1 hour and then filtered. The filtrate was concentrated and purified by reverse phase C18 column chromatography (MeCN:H₂O) to give the desired product as a yellow solid (2.7 g, 55%). ESI-MS m/z: 548.4 [M+H]⁺.

Examples 6 and 7 Step c

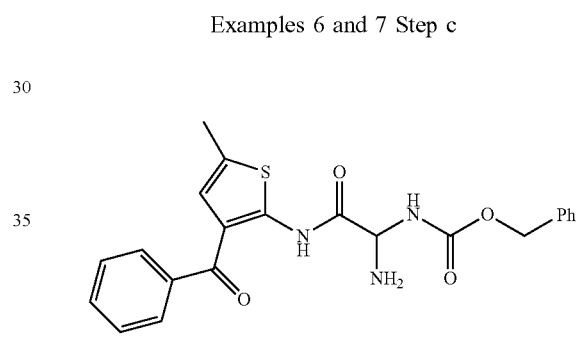

The compound from step b (2.7 g, 5.1 mmol) was dissolved in THF (30 mL) and cooled with ice bath. A solution of ammonia water (5 mL) in THF (10 mL) was added dropwise. The mixture was stirred at this temperature for 1 hour and then concentrated. The residue was purified by reverse phase C18 column chromatography (MeCN:H₂O) to give the desired product as a yellow solid (1.6 g, 74%). ESI-MS m/z: 446.4 [M+H]⁺.

Examples 6 and 7 Step d

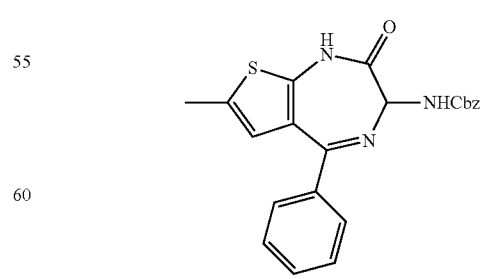

The compound from step c (10 g, 23.6 mmol) was dissolved in AcOH (100 mL) and AcONH₄ (9.1 g, 0.12 mol) was added. The mixture was stirred at rt for 72 hours and then concentrated. The residue was dissolved in EA (500 mL) and washed with water (100 mL×2) and brine (200 mL). The organic phase was dried over anhydrous Na$_2$SO$_4$ and concentrated. The residue was purified by silica gel chromatography (PE:EA=1:1) to give the desired product as a yellow solid (900 mg, 9%). ESI-MS m/z: 406.2 [M+H]$^+$.

Examples 6 and 7 Step e

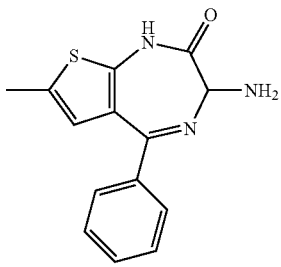 [SMILES: Cc1cc2c(s1)NC(=O)C(N)N=C2c1ccccc1]

The compound from step d (900 mg, 2.22 mmol) was dissolved in HBr/HOAc (10 mL) and heated to 70° C. for 20 minutes. The mixture was cooled to rt and Et$_2$O was added. The precipitate was filtered and collected and then dissolved in water. Ammonium hydroxide was added to adjust the pH to 8. The mixture was filtered and the filter was collected and dried to give the desired product as a light yellow solid (400 mg, 66%). ESI-MS m/z: 272.2 [M+H]$^+$.

Examples 6 and 7 Step f

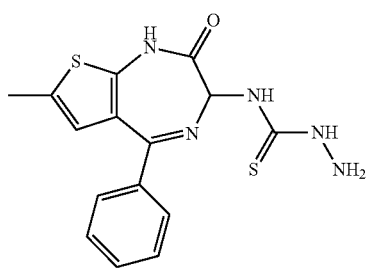 [SMILES: Cc1cc2c(s1)NC(=O)C(NC(=S)NN)N=C2c1ccccc1]

TCDI (196.8 mg, 1.1 mmol) was dissolved in DMF (5 mL) and cooled with ice bath. The compound from step e (200 mg, 0.74 mmol) was added. The mixture was stirred at this temperature for 20 minutes and 98% hydrazine hydrate (1 mL) was added. The mixture was stirred for 1 hour and then purified by reverse phase C18 column chromatography (MeCN:H$_2$O) to give the desired product as a yellow solid (180 mg, 70%). ESI-MS m/z: 346.1 [M+H]$^+$.

Examples 6 and 7 Step g

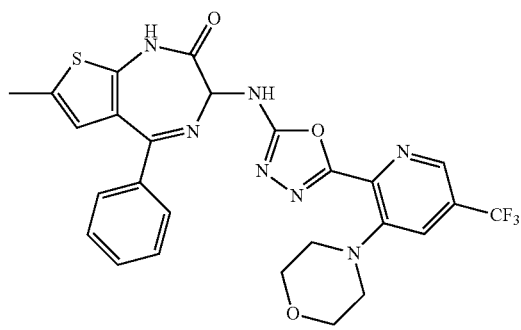 [SMILES: Cc1cc2c(s1)NC(=O)C(Nc1nnc(-c3ncc(C(F)(F)F)cc3N3CCOCC3)o1)N=C2c1ccccc1]

The compound from step f (180 mg, 0.52 mmol) and 3-morpholino-5-(trifluoromethyl)picolinic acid from Example 4 step h (287 mg, 1.04 mmol) was dissolved in DMF (5 mL). HOBt (250 mg, 1.04 mmol) and EDCI (498 mg, 2.60 mmol) was added. The mixture was stirred at rt for 2 hours and then heated to 60° C. for 2 hours. The mixture was cooled to rt and water (20 mL) added. The mixture was extracted with EA (30 mL×3) and the combined organic phase was dried over anhydrous Na$_2$SO$_4$ and concentrated. The residue was purified by reverse phase C18 column chromatography (MeCN:H$_2$O) to give the desired product as a yellow solid (80 mg, 27%). ESI-MS m/z: 570.4 [M+H]$^+$.

Examples 6 and 7 Step h

Example 6

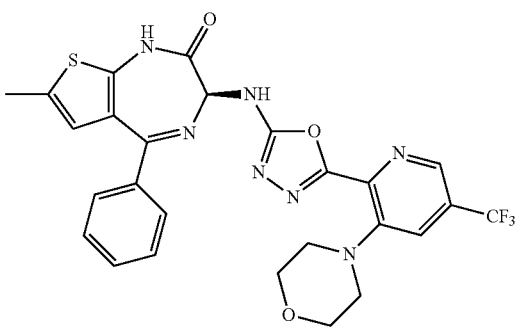

Example 7

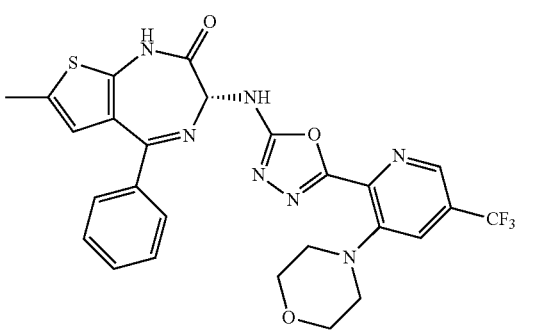

The racemic compound from step g (80 mg, 0.14 mmol) was separated by Chiral Prep-HPLC to give Example 6 (23 mg, 28%) and Example 7 (24 mg, 28%) both as yellow solids. Example 6: ESI-MS m/z: 570.2 [M+H]$^+$. $^1$H NMR (300 MHz, DMSO-d$_6$) δ $^1$H NMR (300 MHz, DMSO-d$_6$) δ 2.44 (d, J=1.2 Hz, 3H), 3.08-3.11 (m, 4H), 3.66-3.80 (m, 4H), 5.32 (d, J=8.4 Hz, 1H), 6.67 (d, J=1.4 Hz, 1H), 7.46-7.55 (m, 3H), 7.58-7.68 (m, 2H), 7.79-7.98 (m, 1H), 8.70 (d, J=1.8 Hz, 1H), 9.39 (d, J=8.5 Hz, 1H), 11.63 (s, 1H). Example 7: ESI-MS m/z: 570.3 [M+H]$^+$. $^1$H NMR (300 MHz, DMSO-d$_6$) δ 2.44 (d, J=1.2 Hz, 3H), 3.08-3.11 (m, 4H), 3.74-3.79 (m, 4H), 5.32 (d, J=8.4 Hz, 1H), 6.67 (d, J=1.4 Hz, 1H), 7.46-7.55 (m, 3H), 7.62-7.65 (m, 2H), 7.86-7.96 (m, 1H), 8.70 (d, J=1.8 Hz, 1H), 9.39 (d, J=8.5 Hz, 1H), 11.63 (s, 1H).

Examples 8 and 9

Example 8

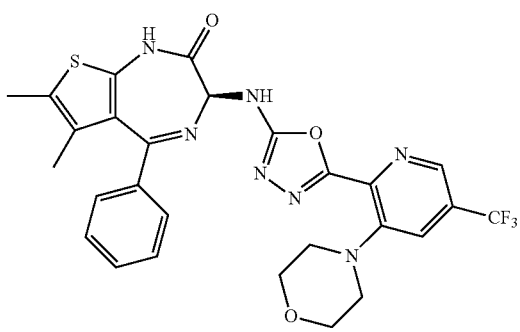

Example 9

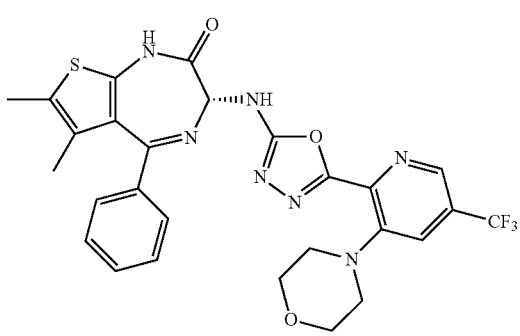

Examples 8 and 9 Step a

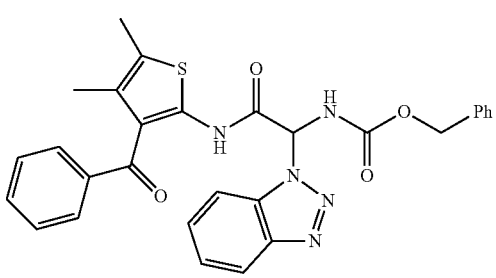 [SMILES: Cc1sc(NC(=O)C(NC(=O)OCc2ccccc2)n2nnc3ccccc32)c(C(=O)c2ccccc2)c1C]

Oxalyl chloride (1.37 g, 10.85 mmol) was added to the solution of the acid from Example 1 step a (3.39 g, 10.14 mmol) in the DMF (2 mL) and THF (20 mL) at 0° C. After stirring for 1 hour, the (2-amino-4,5-dimethylthiophen-3-yl)(phenyl)methanone (2.0 g, 8.68 mmol) and PPY (2.56 g, 17.2 mmol) in DCM (20 mL) was added. The mixture was stirred at rt for 1 hour and then concentrated. The reaction mixture was poured into water and extracted with EA (3×100 mL). The organic layer was dried over $Na_2SO_4$. The residue was concentrated to give the desired compound as a yellow solid (2.1 g). ESI-MS m/z: 540.2 [M+H]$^+$.

Examples 8 and 9 Step b

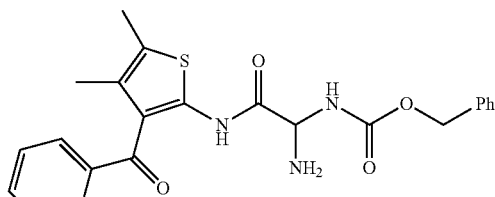

To a stirring solution of the compound from step a (2.1 g, 3.89 mmol) was added to ($NH_3 \cdot H_2O$:MeOH=3:1) (12 mL). The resulting solution was stirred at rt for 1 hour. The reaction mixture was concentrated and used directly in the next step (2.5 g). ESI-MS m/z: 460.4 [M+Na]$^+$.

Examples 8 and 9 Step c

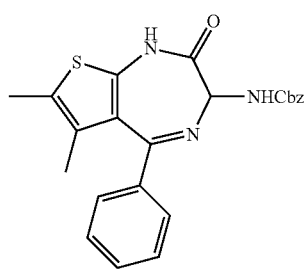 [SMILES: Cc1sc2c(c1C)C(c1ccccc1)=NC(NC(=O)OCc1ccccc1)C(=O)N2]

To a stirring solution of the compound from step b (2.5 g, 5.72 mmol) was added to the $NH_4OAc$ (1.5 g, 0.19 mol) in the AcOH (30 mL) and then stirred overnight. The crude product was purified by reverse phase C18 column chromatography (MeCN:$H_2O$) to give the desired product as a white solid (1.35 g, 56%). ESI-MS m/z: 420.1 [M+H]$^+$.

Examples 8 and 9 Step d

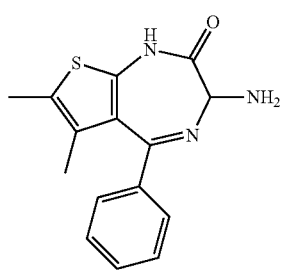 [SMILES: Cc1sc2c(c1C)C(c1ccccc1)=NC(N)C(=O)N2]

The compound from step c (1.35 g, 3.22 mmol) in HBr/AcOH (20 mL) was stirred at 70° C. for 20 mins. The reaction mixture was poured into ether and filtered. The obtained solid was basified by ammonium hydroxide and filtered to give the desired compound as a yellow solid (441 mg, 48%). ESI-MS m/z: 286.0 [M+H]$^+$.

Examples 8 and 9 Step e

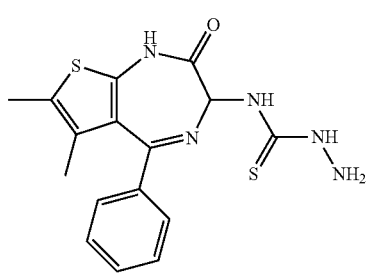 [SMILES: Cc1sc2c(c1C)C(c1ccccc1)=NC(NC(=S)NN)C(=O)N2]

To a stirring solution of the compound from step d (441 mg, 1.54 mmol) in the DMF (15 mL) was added TCDI (413 mg, 2.31 mmol). After stirring for 1 hour, the $NH_2NH_2.H_2O$ (5 mL) was added and then it was stirred overnight at room temperature. The crude product was purified by reverse phase C18 column chromatography ($MeCN:H_2O$) to give the desired product as yellow oil (450 mg, 81%). ESI-MS m/z: 360.0 [M+H]+.

Examples 8 and 9 Step f

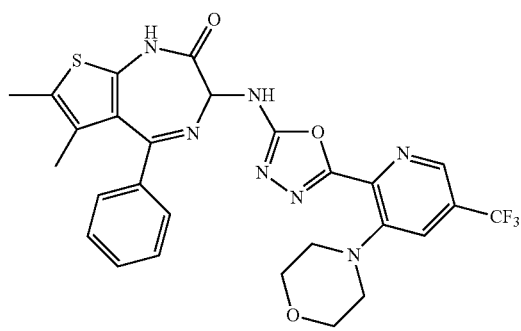 [SMILES: Cc1sc2c(c1C)C(c1ccccc1)=NC(Nc1nnc(-c3ncc(C(F)(F)F)cc3N3CCOCC3)o1)C(=O)N2]

To a stirring solution of the compound from step e (450 mg, 1.25 mmol) in DMF (10 mL) at rt was added 3-morpholino-5-(trifluoromethyl)picolinic acid from Example 4 step h (517 mg, 1.85 mmol) EDCI (253 mg, 1.32 mmol) and HOBt (200 mg, 2.5 mmol). The resulting solution was stirred at 60° C. for 6 hours. Then the crude product was purified by purified by TLC and Prep-HPLC to give the desired product (130 mg, 18%). ESI-MS m/z: 584.0 [M+H]+.

Examples 8 and 9 Step g

Example 8

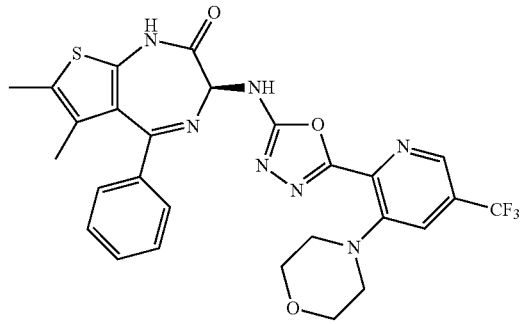

Example 9

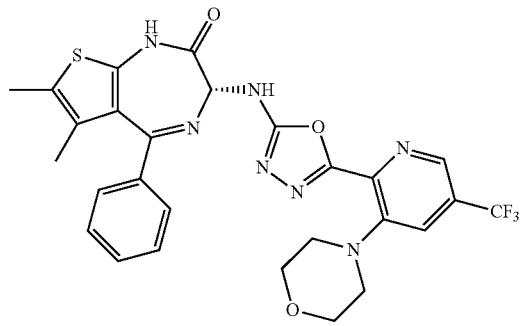

The racemic compound from step f (130 mg, 0.22 mmol) was separated by chiral SFC with CHIRALART Amylose-SA2*25 cm, 5 um KSA99S05-2520WX13534 to give Example 8 as a white solid (45 mg, 35%) and Example 9 as a yellow solid (52 mg, 40%). Example 8: ESI-MS m/z: 584.0 [M+H]+. $^1$H NMR (300 MHz, DMSO-$d_6$) δ 1.58 (3 H, s), 2.31 (3 H, s), 3.08 (4 H, m), 3.74 (4 H, t), 5.30 (1 H, d), 7.48 (5 H, d), 7.89 (1 H, s), 8.68 (1 H, s), 9.38 (1 H, d), 11.47 (1 H, s). Example 9: ESI-MS m/z: 584.0 [M+H]+. $^1$H NMR (300 MHz, DMSO-$d_6$) δ1.58 (3 H, s), 2.31 (3 H, s), 3.08 (4 H, t), 3.74 (4 H, t), 5.30 (1 H, d), 7.48 (5 H, d), 7.89 (1 H, d), 8.68 (1H, m), 9.38 (1 H, d), 11.48 (1 H, s).

Examples 10-15 can be prepared by using a procedure similar to that used to prepare Examples 4-9.

| Example | Structure |
| --- | --- |
| 10 | 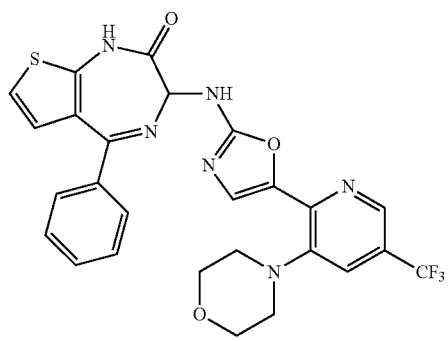 [SMILES: O=C1Nc2sccc2C(c2ccccc2)=NC1Nc1ncc(-c2ncc(C(F)(F)F)cc2N2CCOCC2)o1] |
| 11 | 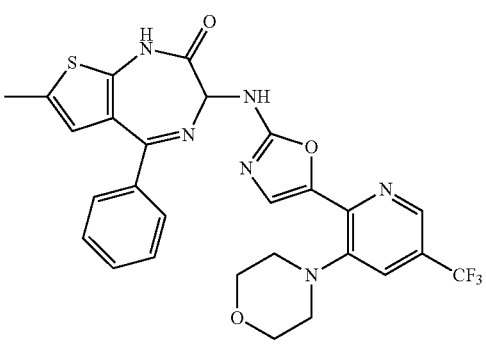 [SMILES: Cc1cc2c(s1)NC(=O)C(Nc1ncc(-c3ncc(C(F)(F)F)cc3N3CCOCC3)o1)N=C2c1ccccc1] |

| Example | Structure |
|---------|-----------|
| 12 | [structure] |
| 13 | [structure] |
| 14 | [structure] |
| 15 | [structure] |

Assays
Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focusses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days.

Following extensive parameter testing, the final assay is run as follows: HEp-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% FBS). 2-fold serial dilutions of control and test compounds are added to the wells in duplicate in a total volume of 25 µL. Viral stock is then added to the wells in a volume of 25 µL, bringing the total volume of each well to 100 µL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 µL of growth media to act as a thermal and evaporative moat around the test wells. Following a 4-day incubation period, the plates are read using ATPlite (50 uL added per well), which quantifies the amount of ATP (a measure of cell health) present in each well. Assay plates are read using the Envision luminometer. These data are used to calculate the $EC_{50}$ of each compound. $EC_{50}$ ranges are as follows: A<0.4 µM; B 0.4-0.8 µM; C>0.8 µM.

TABLE 2

Summary of Activities

| Example | Human RSV-A ("Long" strain) $EC_{50}$ |
|---------|----------------------------------------|
| 1 | C |
| 2 | C |
| 3 | C |
| 4 | B |
| 5 | B |
| 6 | A |
| 7 | C |
| 8 | B |
| 9 | C |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I), or a pharmaceutically acceptable salt thereof:

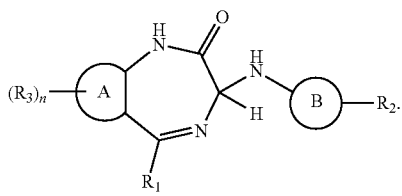

(I)

wherein:
A is heteroaryl;
B is selected from the group consisting of:

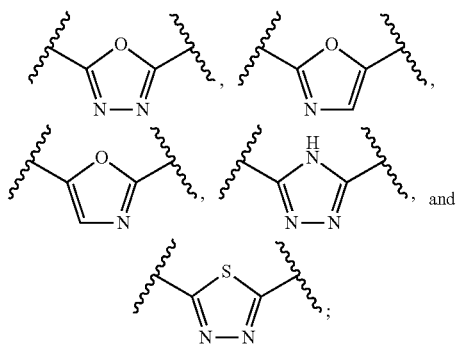

$R_1$ is optionally substituted aryl or optionally substituted heteroaryl;
$R_2$ is selected from the group consisting of:
1) optionally substituted —$C_3$-$C_{12}$ cycloalkyl;
2) optionally substituted —$C_3$-$C_{12}$ cycloalkenyl;
3) optionally substituted 3- to 12-membered heterocyclyl;
4) optionally substituted aryl;
5) optionally substituted heteroaryl;
6) —$NR_{13}R_{14}$;
7) —CO—$NR_{13}R_{14}$; and
8) —$SO_2$—$NR_{13}R_{14}$;
each $R_3$ is the same or different and independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, optionally substituted —NH$C_1$-$C_8$ alkyl, optionally substituted —S—(—$C_1$-$C_8$ alkyl), optionally substituted —$SO_2$—(—$C_1$-$C_8$ alkyl), —optionally substituted —$SO_2$—NH—(—$C_1$-$C_8$ alkyl), optionally substituted —NH—$SO_2$—(—$C_1$-$C_8$ alkyl), —$CO_2R_{11}$, —$NR_{13}R_{14}$, and —CO—$NR_{13}R_{14}$;
each $R_{11}$ is independently selected from the group consisting of:
1) optionally substituted —$C_1$-$C_8$ alkyl;
2) optionally substituted —$C_2$-$C_8$ alkenyl;
3) optionally substituted —$C_2$-$C_8$ alkynyl;
4) optionally substituted —$C_3$-$C_8$ cycloalkyl;
5) optionally substituted —$C_3$-$C_8$ cycloalkenyl;
6) optionally substituted 3- to 8-membered heterocycloalkyl;
7) optionally substituted aryl; and
8) optionally substituted heteroaryl; and $R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted —$C_1$-$C_8$-alkoxy, —$C(O)R_{11}$, —$S(O)_2R_{11}$, and —$S(O)_2NHR_{11}$; alternatively, $R_{13}$ and $R_{14}$ are taken together with the nitrogen atom to which they attached to form a heterocyclic ring; and n is 0 k, where k is the total number of CH and NH groups in group A when A is unsubstituted.

2. The compound of claim 1, represented by Formula (Ia) or (Ib), or a pharmaceutically acceptable salt thereof:

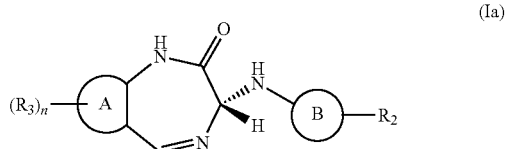

(Ia)

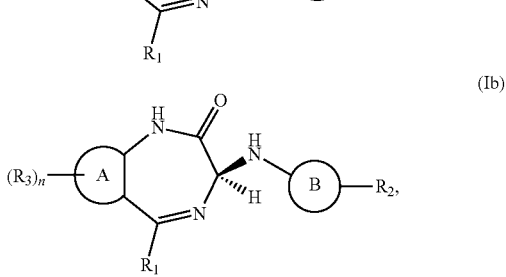

(Ib)

wherein $R_1$, $R_2$, $R_3$, A, B and n are as defined in claim 1.

3. The compound of claim 1, represented by Formula (IIa) or (IIb), or a pharmaceutically acceptable salt thereof:

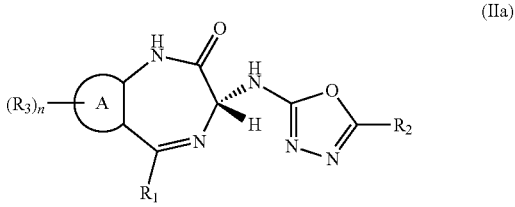

(IIa)

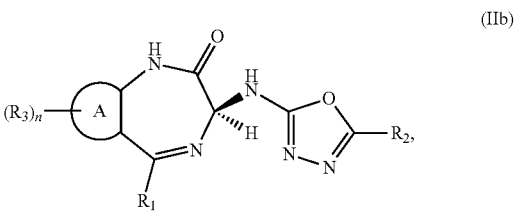

(IIb)

wherein $R_1$, $R_2$, $R_3$, A, and n are as defined in claim 1.

4. The compound of claim 1, represented by one of Formulas (III-1)~(III-3), (IIIa-1)~(IIIa-3), and (IIIb-1)~(IIIb-3), or a pharmaceutically acceptable salt thereof:

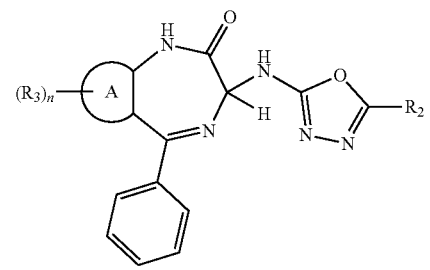
III-1
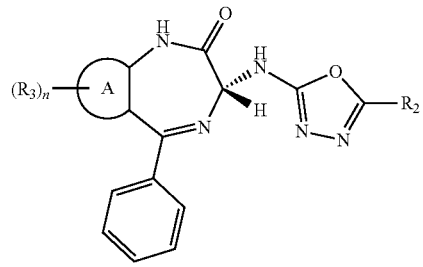
IIIa-1
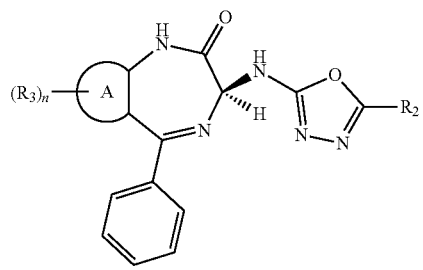
IIIb-1
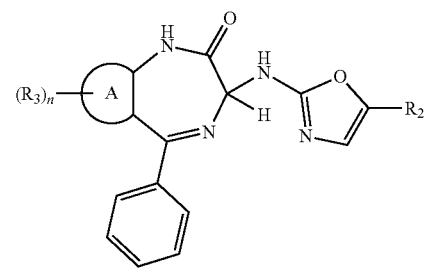
III-2
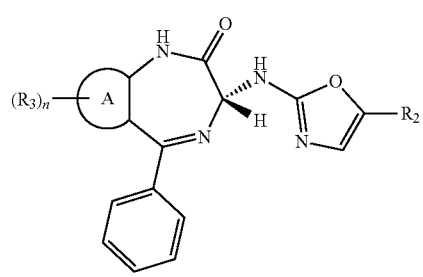
IIIa-2
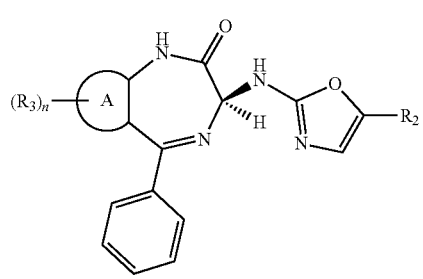
IIIb-2
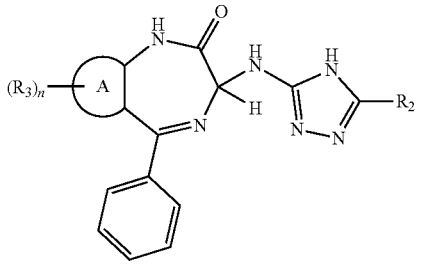
III-3
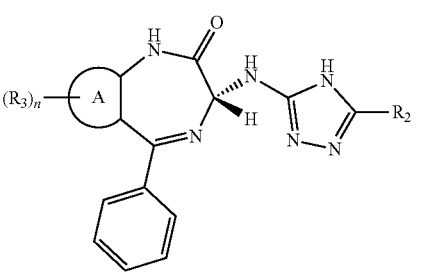
IIIa-3
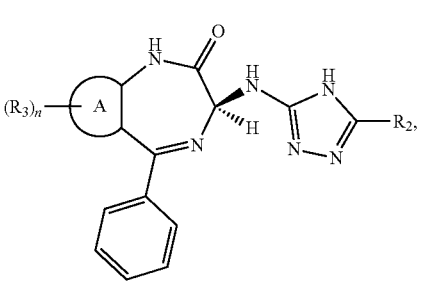
IIIb-3
wherein $R_2$, $R_3$, A, and n are as defined in claim 1.
5. The compound of claim 1, represented by Formula (IVa-1), (IVa-2), (IVb-1) or (IVb-2), or a pharmaceutically acceptable salt thereof:
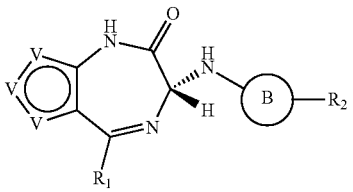
(IVa-1)
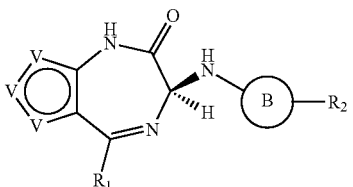
(IVa-2)
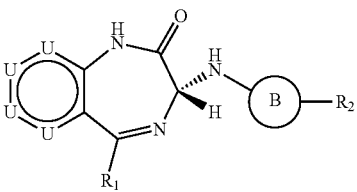
(IVb-1)

(IVb-2)

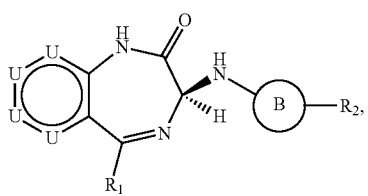

wherein one V is S, O, or NR$_{15}$, the other two Vs are independently CR$_{15}$ or N; one U is N, another U is CR$_{15}$, and the other two Us are independently CR$_{15}$ or N; R$_{15}$ is H or R$_3$; and R$_1$, R$_2$, R$_3$, and B are as defined in claim 1.

6. The compound of claim 1, wherein A is selected from one of the following by removal of hydrogen atoms from two adjacent ring carbon atoms:

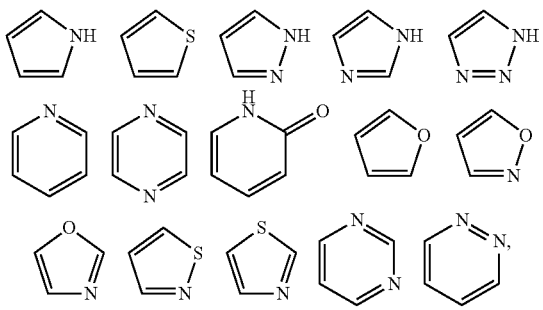

wherein each of the above shown groups is optionally substituted.

7. The compound of claim 1, wherein R$_2$ is selected from one of the following by removal of one hydrogen atom:

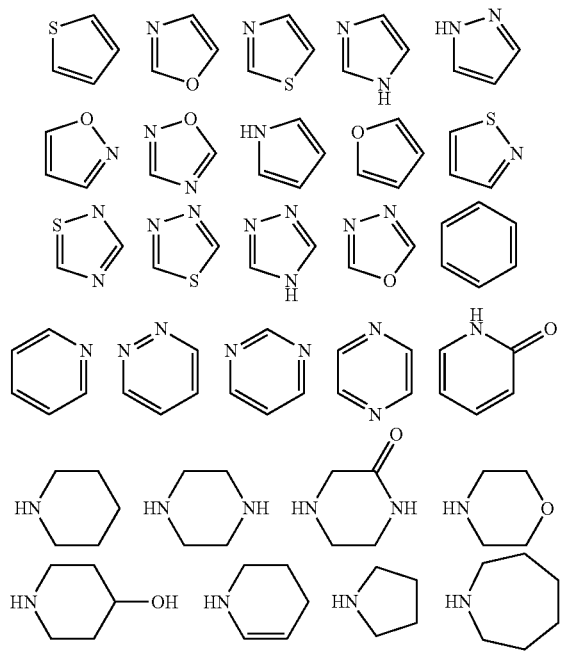

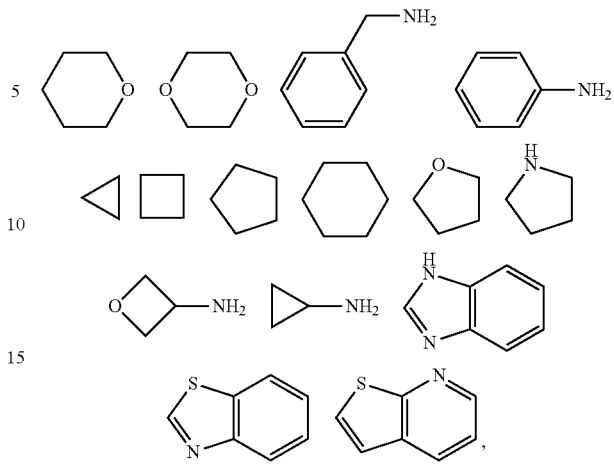

wherein each of the above shown is optionally substituted.

8. The compound of claim 1, wherein R$_2$ is selected from the groups set forth in Table 1:

TABLE 1

| Entry | R$_2$ |
|---|---|
| 1 | phenyl |
| 2 | 2-fluorophenyl |
| 3 | 3-fluorophenyl |
| 4 | 4-fluorophenyl |
| 5 | 2,4-difluorophenyl |
| 6 | 4-pyridyl |

TABLE 1-continued
| Entry | R₂ |
|---|---|
| 7 | 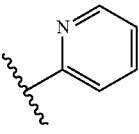 [SMILES: *c1ccccn1] |
| 8 | 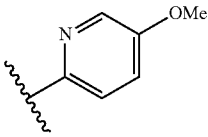 [SMILES: *c1ccc(OC)cn1] |
| 9 | 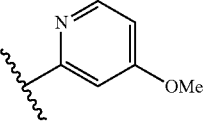 [SMILES: *c1cc(OC)ccn1] |
| 10 | 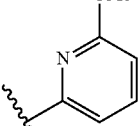 |
| 11 | 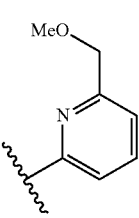 [SMILES: *c1cccc(COC)n1] |
| 12 | 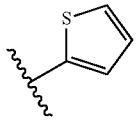 [SMILES: *c1cccs1] |
| 13 | 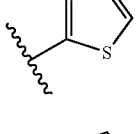 |
| 14 | 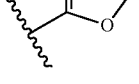 |
| 15 | 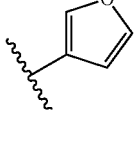 |
| 16 | 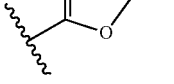 |
TABLE 1-continued
| Entry | R₂ |
|---|---|
| 17 | 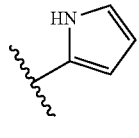 |
| 18 | 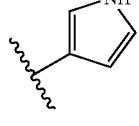 |
| 19 | 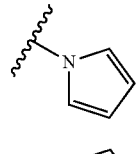 |
| 20 | 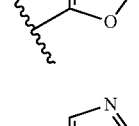 |
| 21 | 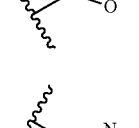 |
| 22 | 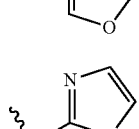 |
| 23 | 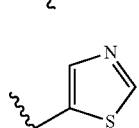 |
| 24 | 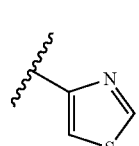 |
| 25 | 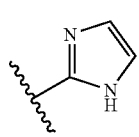 |
| 26 | 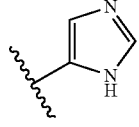 [SMILES: *c1cnc[nH]1] |
| 27 | 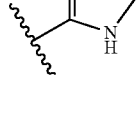 |

TABLE 1-continued
| Entry | R₂ |
|---|---|
| 28 | 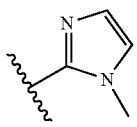 |
| 29 | 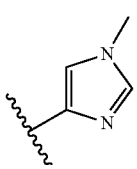 [SMILES: *c1cn(C)cn1] |
| 30 | 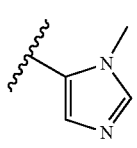 [SMILES: *c1cncn1C] |
| 31 | 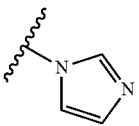 [SMILES: *n1ccnc1] |
| 32 | 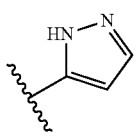 |
| 33 | 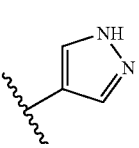 [SMILES: *c1cn[nH]c1] |
| 34 | 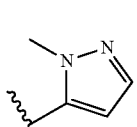 |
| 35 | 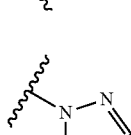 |
| 36 | 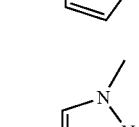 |
| 37 | 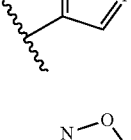 |
| 38 | 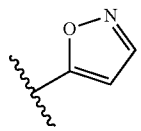 [SMILES: *c1ccno1] |
| 39 | 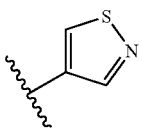 [SMILES: *c1cnsc1] |
| 40 | 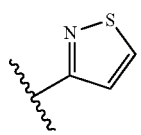 |
| 41 | 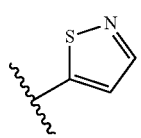 |
| 42 | 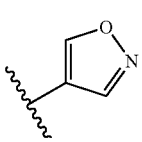 [SMILES: *c1cnoc1] |
| 43 | 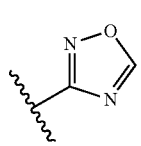 [SMILES: *c1ncon1] |
| 44 | 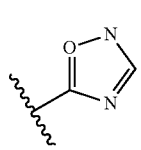 |
| 45 | 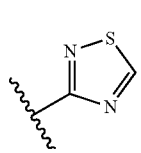 |
| 46 | 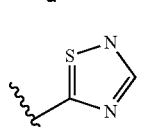 |
| 47 | 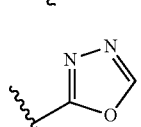 |
| 48 | 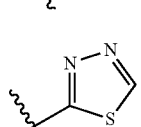 |

TABLE 1-continued
| Entry | R₂ |
|---|---|
| 49 | 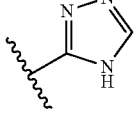 |
| 50 | 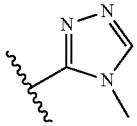 |
| 51 | 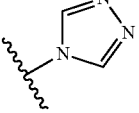 |
| 52 | 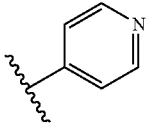 [SMILES: *c1ccncc1] |
| 53 | 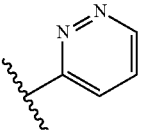 [SMILES: *c1cccnn1] |
| 54 | 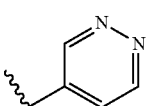 |
| 55 | 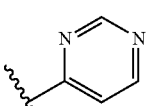 |
| 56 | 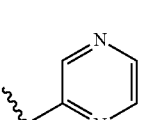 |
| 57 | 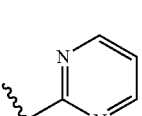 |
| 58 | 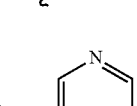 |
| 59 | 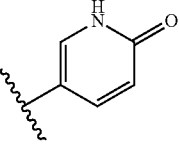 [SMILES: *c1ccc(=O)[nH]c1] |
| 60 | 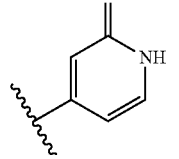 |
| 61 | 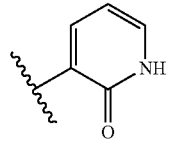 [SMILES: *c1ccc[nH]c1=O] |
| 62 | 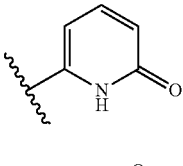 |
| 63 | 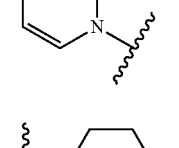 |
| 64 | 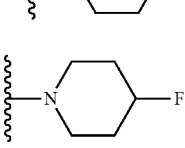 |
| 65 | 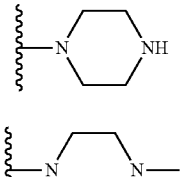 |
| 66 | 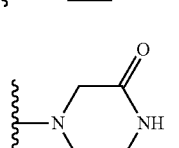 |
| 67 | 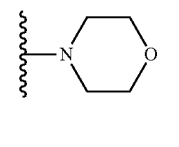 |
| 68 |  |
| 69 |  |

TABLE 1-continued
| Entry | R₂ |
|---|---|
| 70 | 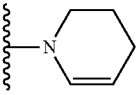 |
| 71 | 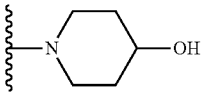 |
| 72 | 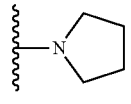 |
| 73 | 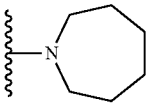 |
| 74 | 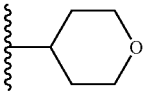 |
| 75 | 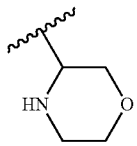 |
| 76 | 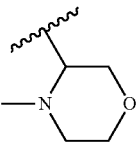 [SMILES: *C1COCCN1C] |
| 77 | 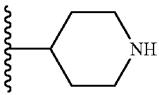 |
| 78 | 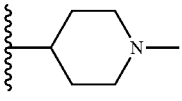 |
| 79 | 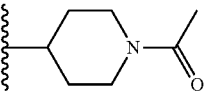 |
| 80 | 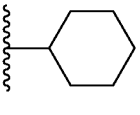 |
| 81 | 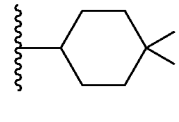 |
| 82 |  |
| 83 | 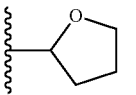 |
| 84 | 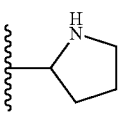 |
| 85 | 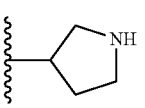 |
| 86 | 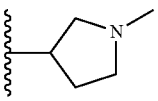 [SMILES: *C1CCN(C)C1] |
| 87 | 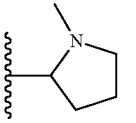 |
| 88 | 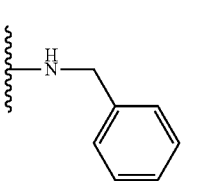 [SMILES: *NCc1ccccc1] |
| 89 | 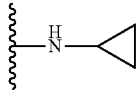 |
| 94 | 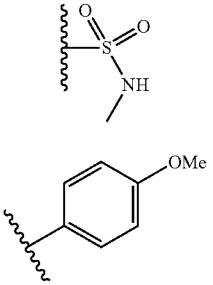 |
| 95 | 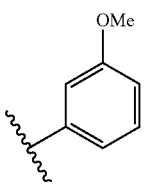 [SMILES: *c1cccc(OC)c1] |
| 96 | 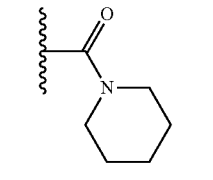 [SMILES: *C(=O)N1CCCCC1] |
| 97 |  |

TABLE 1-continued
| Entry | R$_2$ |
|---|---|
| 98 | 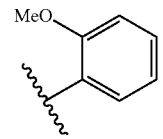 2-MeO-phenyl |
| 99 | 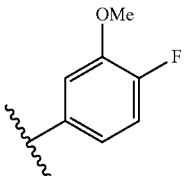 [SMILES: *c1ccc(F)c(OC)c1] 3-OMe-4-F-phenyl |
| 100 | 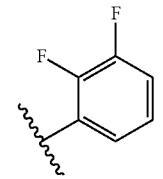 [SMILES: *c1cccc(F)c1F] 2,3-diF-phenyl |
| 101 | 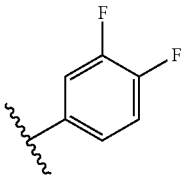 [SMILES: *c1ccc(F)c(F)c1] 3,4-diF-phenyl |
| 102 | 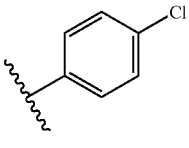 4-Cl-phenyl |
| 103 | 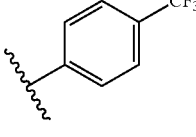 4-CF$_3$-phenyl |
| 104 | 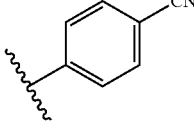 4-CN-phenyl |
| 105 | 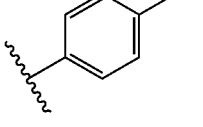 4-OCF$_3$-phenyl |
| 106 | 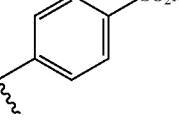 4-SO$_2$Me-phenyl |
TABLE 1-continued
| Entry | R$_2$ |
|---|---|
| 107 | 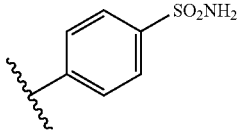 [SMILES: *c1ccc(S(N)(=O)=O)cc1] 4-SO$_2$NH$_2$-phenyl |
| 108 | 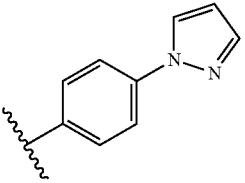 [SMILES: *c1ccc(-n2cccn2)cc1] 4-(1-pyrazolyl)-phenyl |
| 109 | 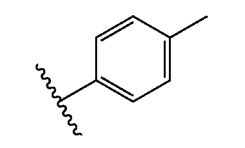 [SMILES: *c1ccc(C)cc1] 4-Me-phenyl |
| 110 | 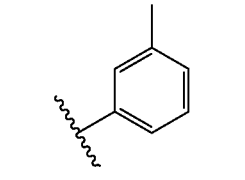 [SMILES: *c1cccc(C)c1] 3-Me-phenyl |
| 111 | 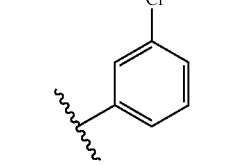 3-Cl-phenyl |
| 112 | 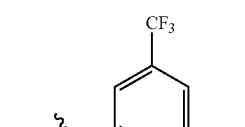 3-CF$_3$-phenyl |
| 113 | 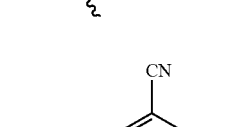 3-CN-phenyl |
| 114 | 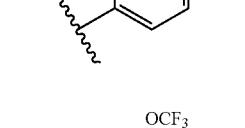 3-OCF$_3$-phenyl |

TABLE 1-continued
| Entry | R₂ |
|---|---|
| 115 | 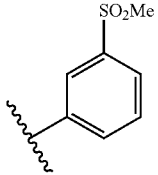 [SMILES: *c1cccc(S(C)(=O)=O)c1] SO₂Me (phenyl) |
| 116 | 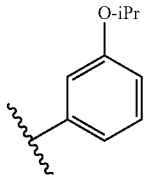 O-iPr (phenyl) |
| 117 | 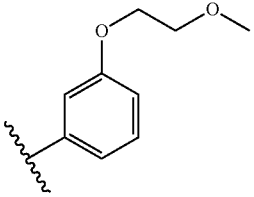 [SMILES: *c1cccc(OCCOC)c1] O-CH₂CH₂-OMe (phenyl) |
| 118 | 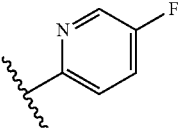 [SMILES: *c1ccc(F)cn1] 5-F pyridyl |
| 119 | 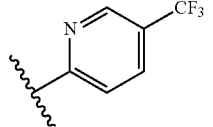 [SMILES: *c1ccc(C(F)(F)F)cn1] 5-CF₃ pyridyl |
| 120 | 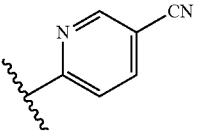 [SMILES: *c1ccc(C#N)cn1] 5-CN pyridyl |
| 121 | 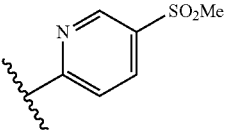 [SMILES: *c1ccc(S(C)(=O)=O)cn1] 5-SO₂Me pyridyl |
| 122 | 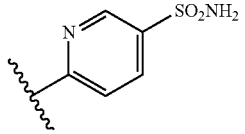 [SMILES: *c1ccc(S(N)(=O)=O)cn1] 5-SO₂NH₂ pyridyl |
| 123 | 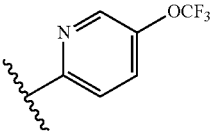 [SMILES: *c1ccc(OC(F)(F)F)cn1] 5-OCF₃ pyridyl |
TABLE 1-continued
| Entry | R₂ |
|---|---|
| 124 | 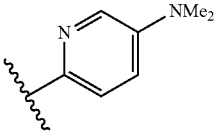 [SMILES: *c1ccc(N(C)C)cn1] 5-NMe₂ pyridyl |
| 125 | 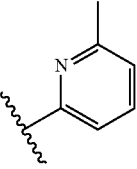 6-Me pyridyl |
| 126 | 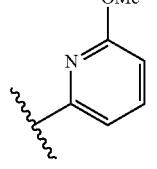 6-OMe pyridyl |
| 127 | 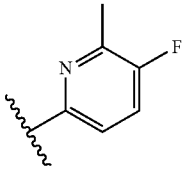 [SMILES: *c1ccc(F)c(C)n1] 6-Me, 5-F pyridyl |
| 128 | 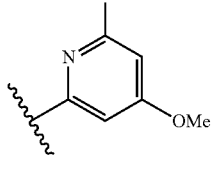 6-Cl, 4-OMe pyridyl |
| 129 | 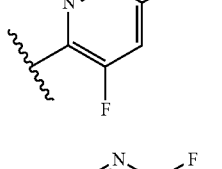 5-OMe, 3-F pyridyl |
| 130 | 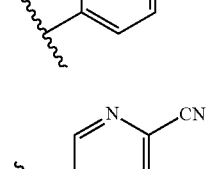 6-F pyridyl |
| 131 | 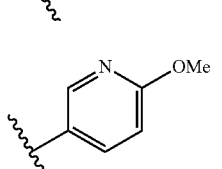 2-CN pyridyl |
| 132 | 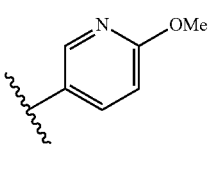 [SMILES: *c1ccc(OC)nc1] 6-OMe pyridyl |

TABLE 1-continued
| Entry | R₂ |
|---|---|
| 133 | 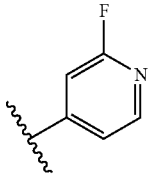 [SMILES: *c1ccnc(F)c1] |
| 134 | 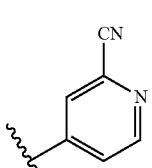 |
| 135 | 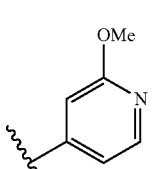 |
| 136 | 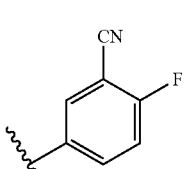 |
| 137 | 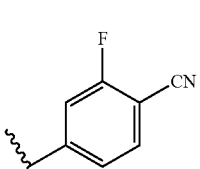 |
| 138 | 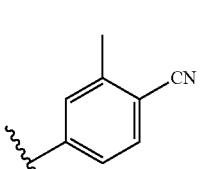 |
| 139 | 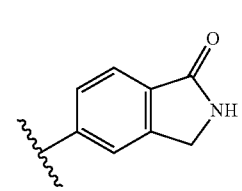 [SMILES: *c1ccc2c(c1)CNC2=O] |
| 140 | 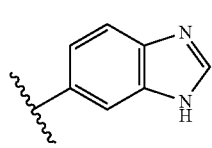 [SMILES: *c1ccc2nc[nH]c2c1] |
TABLE 1-continued
| Entry | R₂ |
|---|---|
| 141 | 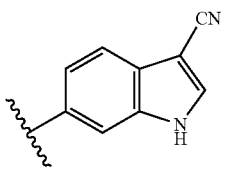 [SMILES: *c1ccc2c(C#N)c[nH]c2c1] |
| 142 | 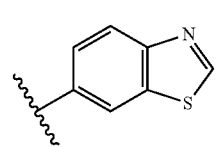 [SMILES: *c1ccc2ncsc2c1] |
| 143 | 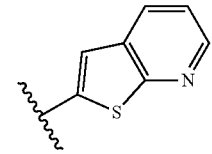 [SMILES: *c1cc2cccnc2s1] |
| 144 | 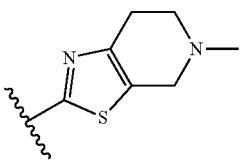 [SMILES: *c1nc2c(s1)CN(C)CC2] |
| 145 | 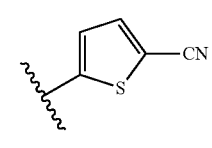 [SMILES: *c1ccc(C#N)s1] |
| 146 | 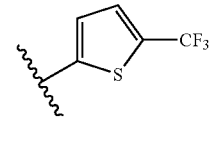 [SMILES: *c1ccc(C(F)(F)F)s1] |
| 148 | 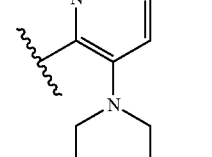 |
| 149 | 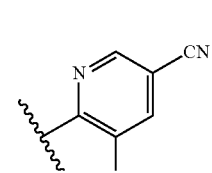 |

TABLE 1-continued
| Entry | R2 |
|---|---|
| 150 | 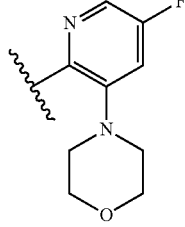 |
| 151 | 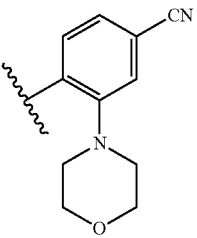 |
| 152 | 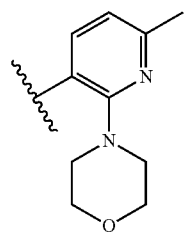 [SMILES: *c1ccc(C)nc1N1CCOCC1] |
| 153 | 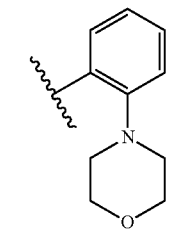 [SMILES: *c1ccccc1N1CCOCC1] |
| 154 | 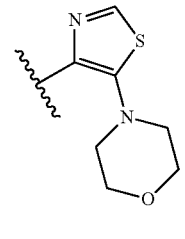 [SMILES: *c1ncsc1N1CCOCC1] |
| 155 | 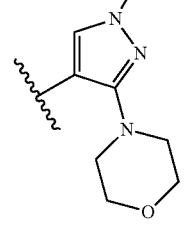 |
| 156 | 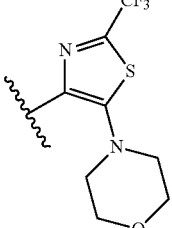 |
| 157 | 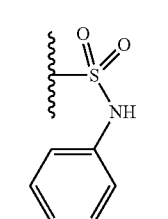 |
| 158 | 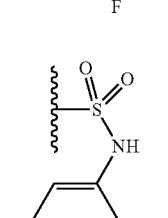 |
| 159 | 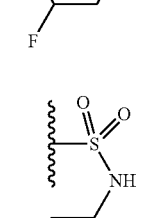 |
| 160 | 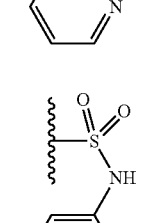 |
| 161 | 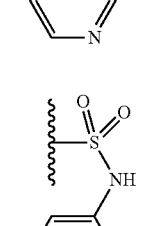 |

TABLE 1-continued
| Entry | R2 |
|---|---|
| 162 | 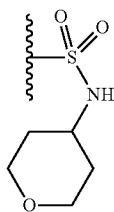 [SMILES: *S(=O)(=O)NC1CCOCC1] |
| 163 | 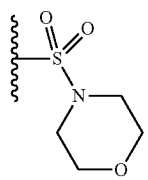 |
| 164 | 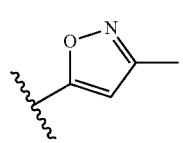 [SMILES: *c1cc(C)no1] |
| 165 | 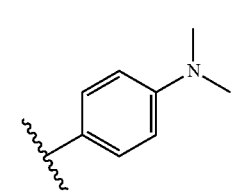 [SMILES: *c1ccc(N(C)C)cc1] |
| 166 | 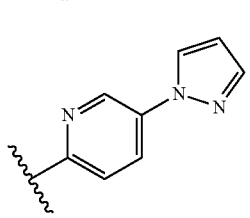 [SMILES: *c1ccc(-n2cccn2)cn1] |
| 167 | 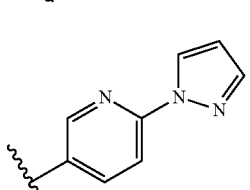 |
| 168 | 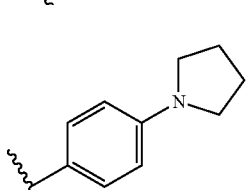 |
| 169 | 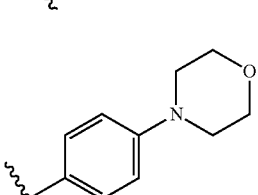 |
TABLE 1-continued
| Entry | R2 |
|---|---|
| 170 | 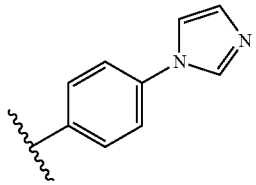 [SMILES: *c1ccc(-n2ccnc2)cc1] |
| 171 | 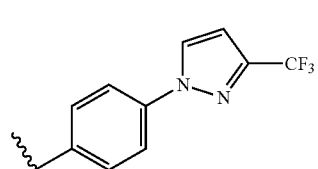 |
| 172 | 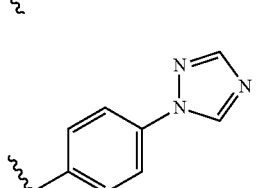 |
| 173 |  |
| 174 |  |
| 175 | 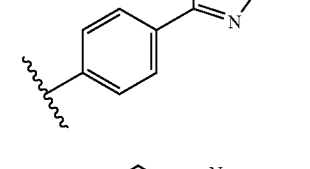 |
| 176 |  |
| 177 |  |

TABLE 1-continued
| Entry | R₂ |
|---|---|
| 179 | 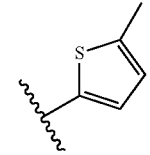 [SMILES: *c1ccc(C)s1] |
| 180 | 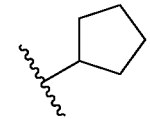 [SMILES: *C1CCCC1] |
| 181 | 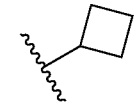 [SMILES: *C1CCC1] |
| 182 | 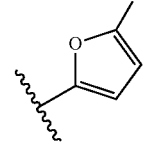 |
| 183 | 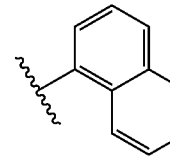 |
| 184 | 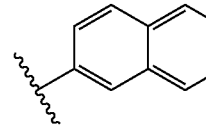 |
| 185 | 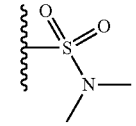 |
| 186 | 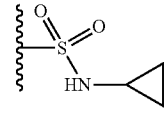 |
9. The compound of claim 1, selected from the compounds set forth below, or a pharmaceutically acceptable salt thereof:
| Compound | Structure |
|---|---|
| 1 | 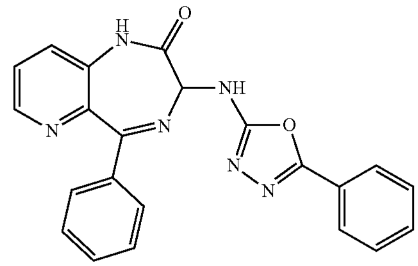 [SMILES: O=C1Nc2cccnc2C(c2ccccc2)=NC1Nc1nnc(-c2ccccc2)o1] |
| 2 | 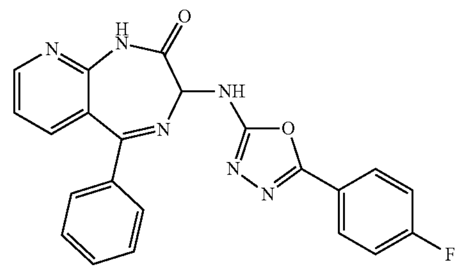 [SMILES: O=C1Nc2ncccc2C(c2ccccc2)=NC1Nc1nnc(-c2ccc(F)cc2)o1] |
| 3 | 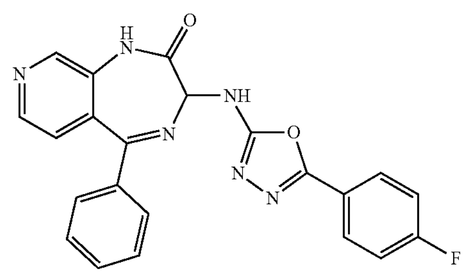 [SMILES: O=C1Nc2cnccc2C(c2ccccc2)=NC1Nc1nnc(-c2ccc(F)cc2)o1] |
| 4 | 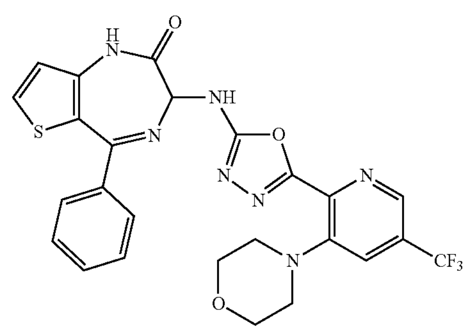 [SMILES: O=C1Nc2ccsc2C(c2ccccc2)=NC1Nc1nnc(-c2ncc(C(F)(F)F)cc2N2CCOCC2)o1] |
| 5 | 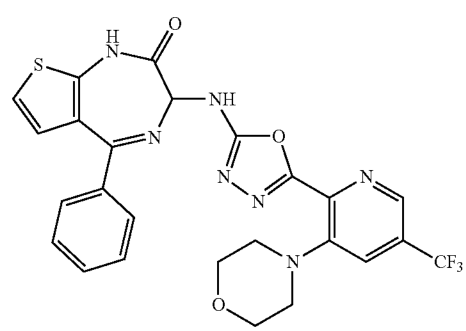 [SMILES: O=C1Nc2sccc2C(c2ccccc2)=NC1Nc1nnc(-c2ncc(C(F)(F)F)cc2N2CCOCC2)o1] |

| Compound | Structure |
|---|---|
| 6 | 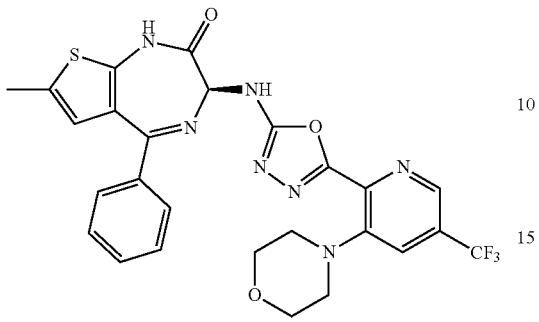 |
| 7 | 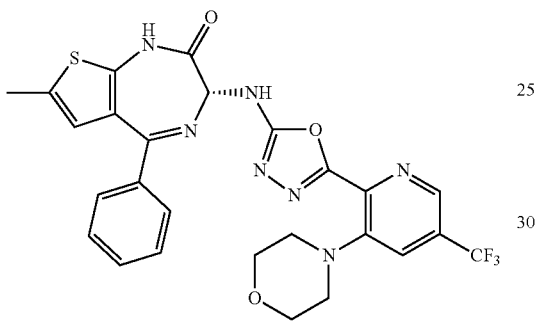 |
| 8 | 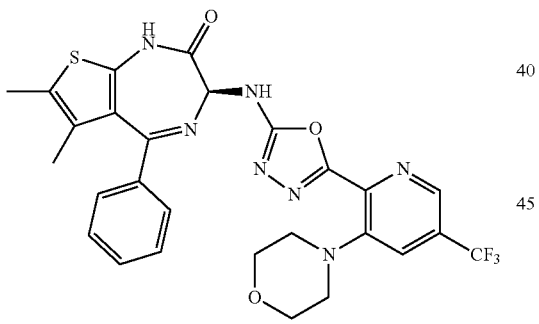 |
| 9 | 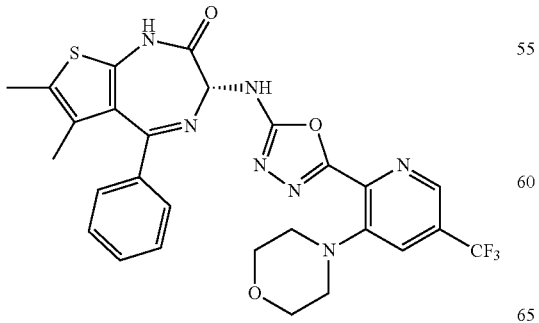 |
| Compound | Structure |
|---|---|
| 10 | 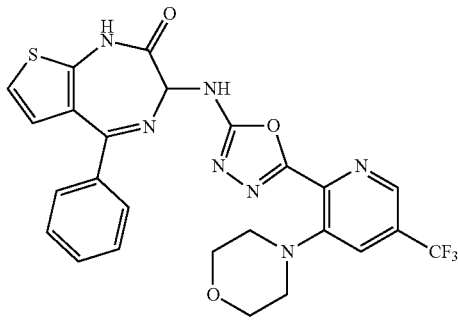 [SMILES: O=C1Nc2sccc2C(c2ccccc2)=NC1Nc1nnc(-c2ncc(C(F)(F)F)cc2N2CCOCC2)o1] |
| 11 | 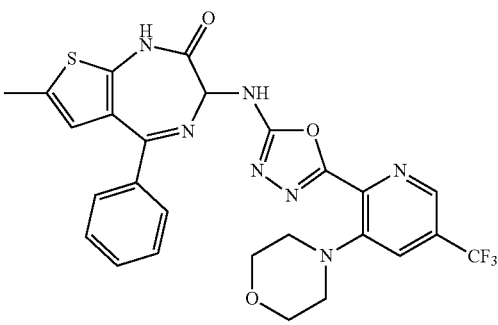 [SMILES: Cc1cc2c(s1)NC(=O)C(Nc1nnc(-c3ncc(C(F)(F)F)cc3N3CCOCC3)o1)N=C2c1ccccc1] |
| 12 | 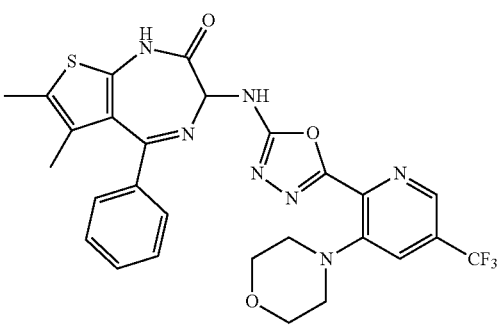 [SMILES: Cc1sc2c(c1C)C(c1ccccc1)=NC(Nc1nnc(-c3ncc(C(F)(F)F)cc3N3CCOCC3)o1)C(=O)N2] |

-continued

| Compound | Structure |
|---|---|
| 13 | 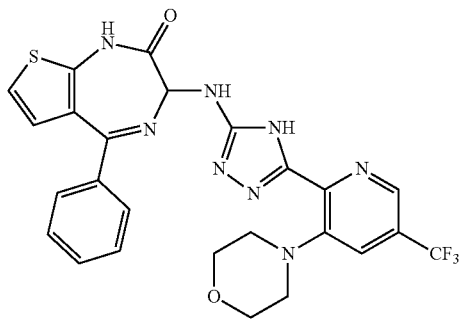 [SMILES: O=C1Nc2sccc2C(c2ccccc2)=NC1Nc1nnc(-c2ncc(C(F)(F)F)cc2N2CCOCC2)[nH]1] |
| 14 | 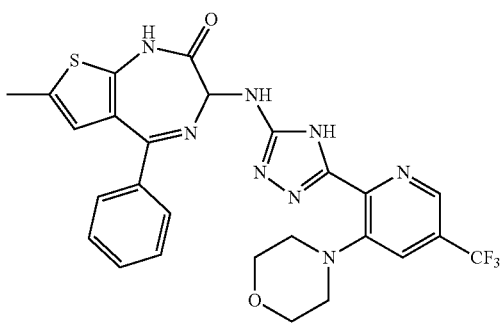 |

-continued

| Compound | Structure |
|---|---|
| 15 | 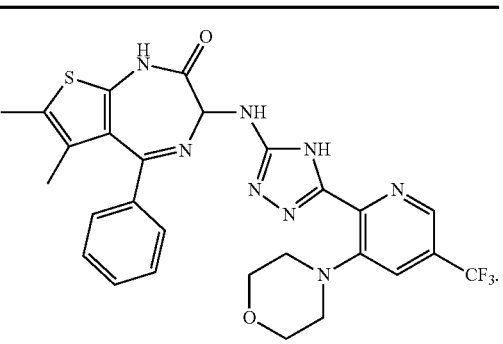 |

10. A pharmaceutical composition, comprising a compound according to claim 1, or a pharmaceutically acceptable salt thereof, and a pharmaceutically acceptable carrier or excipient.

11. A method of treating an RSV infection in a subject in need thereof, comprising administering to the subject a therapeutically effective amount of a compound or a combination of compounds according to claim 1, or a pharmaceutically acceptable salt thereof.

* * * * *